(12) United States Patent
Kobayashi

(10) Patent No.: US 8,582,122 B2
(45) Date of Patent: Nov. 12, 2013

(54) POLISHING MONITORING METHOD, POLISHING METHOD, AND POLISHING MONITORING APPARATUS

(75) Inventor: Yoichi Kobayashi, Tokyo (JP)

(73) Assignee: Ebara Corporation, Tokyo (JP)

( * ) Notice: Subject to any disclaimer, the term of this patent is extended or adjusted under 35 U.S.C. 154(b) by 242 days.

(21) Appl. No.: 13/034,903

(22) Filed: Feb. 25, 2011

(65) Prior Publication Data

US 2011/0216328 A1  Sep. 8, 2011

(30) Foreign Application Priority Data

Mar. 2, 2010  (JP) ................................. 2010-044873
Feb. 4, 2011  (JP) ................................. 2011-022650

(51) Int. Cl.
*G01B 11/06* (2006.01)
(52) U.S. Cl.
USPC .................. 356/630; 356/445; 451/5; 451/6; 451/8
(58) Field of Classification Search
USPC ............ 356/445–448, 630–632; 451/5, 6, 41, 451/288, 287, 398; 438/16, 690–692; 216/85, 88, 89, 90, 91
See application file for complete search history.

(56) References Cited

U.S. PATENT DOCUMENTS

| | | | | |
|---|---|---|---|---|
| 4,669,873 A | * | 6/1987 | Wirz | 356/73 |
| 5,904,609 A | * | 5/1999 | Fukuroda et al. | 451/8 |
| 6,361,646 B1 | * | 3/2002 | Bibby et al. | 156/345.1 |
| 6,511,363 B2 | * | 1/2003 | Yamane et al. | 451/6 |
| 7,252,575 B2 | * | 8/2007 | Kobayashi et al. | 451/6 |
| 7,604,527 B2 | * | 10/2009 | Elledge | 451/6 |
| 2006/0166606 A1 | | 7/2006 | Kobayashi et al. | |
| 2009/0130956 A1 | * | 5/2009 | Ohta et al. | 451/6 |
| 2010/0093260 A1 | * | 4/2010 | Kobayashi et al. | 451/5 |
| 2011/0081829 A1 | | 4/2011 | Ohta et al. | |
| 2012/0009849 A1 | * | 1/2012 | Kimba | 451/6 |
| 2012/0019830 A1 | * | 1/2012 | Kimba | 356/445 |

FOREIGN PATENT DOCUMENTS

| | | |
|---|---|---|
| JP | 2004-154928 | 6/2004 |
| JP | 2009-505847 | 2/2009 |
| WO | 2007/024807 | 3/2007 |

* cited by examiner

*Primary Examiner* — Hoa Pham
(74) *Attorney, Agent, or Firm* — Wenderoth, Lind & Ponack, L.L.P.

(57) ABSTRACT

A method accurately monitors the progress of polishing and accurately detects the polishing end point. The method includes directing light to the substrate during polishing of the substrate, receiving reflected light from the substrate, measuring an intensity of the reflected light at each wavelength, and producing a spectrum indicating a relationship between intensity and wavelength from measured values of the intensity. The method also includes calculating an amount of change in the spectrum per predetermined time, integrating the amount of change in the spectrum with respect to polishing time to obtain an amount of cumulative change in the spectrum, and monitoring the progress of polishing of the substrate based on the amount of cumulative change in the spectrum.

28 Claims, 26 Drawing Sheets

POLISHING MONITORING METHOD, POLISHING METHOD, AND POLISHING MONITORING APPARATUS

BACKGROUND OF THE INVENTION

1. Field of the Invention

The present invention relates to a method of monitoring progress of polishing of a substrate, such as a semiconductor wafer, and more particularly to a method of monitoring progress of substrate polishing based on a change in spectrum obtained from reflected light from the substrate and determining a polishing end point.

The present invention also relates to a polishing monitoring apparatus for performing such a polishing monitoring method.

The present invention further relates to a polishing method for a substrate using such a polishing monitoring method.

2. Description of the Related Art

In fabrication processes of a semiconductor device, several kinds of materials are repeatedly deposited in the form of film on a silicon wafer to form a multilayer structure. It is important for forming such a multilayer structure to planarize a surface of a top layer. Chemical mechanical polishing (CMP) is widely used as one of techniques for achieving such planarization.

The chemical mechanical polishing (CMP) is performed by a polishing apparatus. The polishing apparatus of this type typically includes a polishing table supporting a polishing pad thereon, a top ring for holding a substrate (a wafer with a film formed thereon), and a polishing liquid supply mechanism for supplying a polishing liquid onto the polishing pad. Polishing of a substrate is performed as follows. The top ring presses a surface of the substrate against the polishing pad, while the polishing liquid supply mechanism supplies the polishing liquid onto the polishing pad. In this state, the top ring and the polishing table are rotated independently to provide relative movement between the substrate and the polishing pad, thereby polishing the film that forms the surface of the substrate.

Generally, the polishing apparatus has a polishing end point detection device. An optical polishing end point detection device is one example of such a polishing end point detection device. This device is configured to direct light to the surface of the substrate and to determine a polishing end point based on spectrum of the light reflected from the substrate. For example, a Japanese laid-open patent publication No. 2004-154928 discloses a method in which intensity of the reflected light is processed in order to remove noise components to create characteristic value and the polishing end point is determined based on a distinctive point (i.e., a local maximum point or local minimum point) of temporal variation in the characteristic value.

The spectrum is an arrangement of the light intensity in the order of wavelength. The characteristic value created from the spectrum varies periodically with polishing time, as shown in FIG. 1, and the local maximum point and the local minimum point appear alternately. This phenomenon is due to interference between light waves. Specifically, the light, directed to the substrate, is reflected off an interface between a medium and the film and an interface between the film and a layer beneath the film. The light waves from these interfaces interfere with each other. The manner of interference between the light waves varies depending on the thickness of the film (i.e., a length of an optical path). Therefore, the intensity of the reflected light from the substrate varies periodically in accordance with the thickness of the film. The intensity of the light can also be expressed as a relative value, such as a reflectance or a relative reflectance.

The above-described optical polishing end point detection device counts the number of distinctive points (i.e., the local maximum points or local minimum points) of the temporal variation in the characteristic value during polishing and monitors the polishing progress based on the number of distinctive points. The polishing process is terminated when a predetermined period of time has elapsed from a point of time when the number of distinctive points has reached a predetermined value.

There is also a method of determining the polishing end point by comparing spectrum obtained during polishing with reference spectrum that is prepared in advance, as disclosed in a Japanese laid-open patent publication No. 2009-505847. In this method, the spectrum at each point of time during polishing is compared with the reference spectrum. A point of time when a difference between both spectra satisfies a condition of a target difference is determined to be the polishing end point. The reference spectrum is prepared in advance by polishing a sample substrate of the same type as the substrate to be polished.

A plurality of spectra including the reference spectrum, which are obtained during polishing of the sample substrate, are associated with index values that are correlated with polishing time and rotational speed of the polishing table. The spectra thus obtained are stored as library. Therefore, by comparing spectrum obtained during polishing of another substrate with the spectrum in the library, a polished state of the substrate at each point of time during polishing can be expressed by the index value. This index value can be defined as an index that indicates a film thickness of the substrate relatively or indirectly.

However, in an actual substrate, multiple interconnect layers with different interconnect patterns and multiple dielectric films of different types are piled up to form multilayer interconnect structure. The optical sensor detects the light reflected from a lower dielectric film through a non-interconnect portion of an upper dielectric film. Consequently, if there are variations in thickness of the lower dielectric film and optical constant between substrates, the spectrum is affected by these variations. As a result, the above-described method cannot accurately measure the thickness of the upper film (i.e., the film to be polished) and it is therefore difficult to accurately monitor the progress of polishing. Furthermore, the variations in thickness of the lower dielectric film and optical constant would result in differences in the detected polishing end point between the substrates.

SUMMARY OF THE INVENTION

The present invention has been made in view of the above drawbacks. It is therefore an object of the present invention to provide a method and an apparatus capable of accurately monitoring progress of polishing and capable of detecting an accurate polishing end point. It is also an object of the present invention to provide a polishing method for a substrate using such a polishing monitoring method.

One aspect of the present invention is to provide a method of monitoring progress of polishing of a substrate having a film. The method includes: directing light to the substrate during polishing of the substrate; receiving reflected light from the substrate; measuring intensity of the reflected light at each wavelength; producing spectrum indicating relationship between intensity and wavelength from measured values of the intensity; calculating an amount of change in the spectrum per predetermined time; integrating the amount of change in the spectrum with respect to polishing time to obtain an amount of cumulative change in the spectrum; and monitoring the progress of polishing of the substrate based on the amount of cumulative change in the spectrum.

In a preferred aspect of the present invention, the amount of change in the spectrum is a magnitude of relative change between two spectra produced at two different points of time.

In a preferred aspect of the present invention, the magnitude of relative change is root mean square of difference in the intensity between the two spectra in a predetermined wavelength range.

In a preferred aspect of the present invention, the magnitude of relative change is an average of absolute values of difference in the intensity between the two spectra in a predetermined wavelength range.

In a preferred aspect of the present invention, the amount of change in the spectrum is a rate of change in the spectrum obtained by dividing the magnitude of relative change by a time interval between the two points of time.

In a preferred aspect of the present invention, the amount of change in the spectrum has a plus or minus sign.

In a preferred aspect of the present invention, the spectrum is a spectrum indicating relationship between wavelength and normalized intensity that is obtained by dividing the intensity at each wavelength by an average of the intensity in a predetermined wavelength range.

In a preferred aspect of the present invention, the substrate is a second substrate to be polished after a first substrate having the same structure, and the method further includes: directing light to the first substrate during polishing of the first substrate; receiving reflected light from the first substrate; measuring intensity of the reflected light at each wavelength; producing reference spectrum indicating relationship between intensity and wavelength from measured values of the intensity; calculating an amount of change in the reference spectrum per predetermined time; integrating the amount of change in the reference spectrum with respect to polishing time to obtain an amount of cumulative change in the reference spectrum; and converting the amount of cumulative change in the spectrum with respect to the second substrate into an amount of removed film of the second substrate based on the amount of cumulative change in the reference spectrum, an initial film thickness of the first substrate, and a final film thickness of the first substrate.

In a preferred aspect of the present invention, the method further includes: obtaining an initial film thickness of the second substrate; and converting the amount of removed film into a film thickness of the second substrate by subtracting the amount of removed film from the initial film thickness of the second substrate.

In a preferred aspect of the present invention, the polishing of the substrate is polishing of the substrate for adjusting a height of metal interconnects formed in the substrate.

In a preferred aspect of the present invention, the substrate has the film, a barrier layer formed on the film, and the metal interconnects formed in the film; and the method further comprises determining a removal point of the barrier layer based on the amount of change in the spectrum.

In a preferred aspect of the present invention, the substrate has a surface having steps formed thereon, and the calculating of the amount of cumulative change in the spectrum is started from a point of time when the steps are removed.

In a preferred aspect of the present invention, the method further includes determining a polishing end point of the substrate based on the amount of cumulative change in the spectrum.

Another aspect of the present invention is to provide a method of polishing a substrate having a film. The method includes: polishing the substrate by providing sliding contact between the substrate and a polishing pad; directing light to the substrate during polishing of the substrate; receiving reflected light from the substrate; measuring intensity of the reflected light at each wavelength; producing spectrum indicating relationship between intensity and wavelength from measured values of the intensity; calculating an amount of change in the spectrum per predetermined time; integrating the amount of change in the spectrum with respect to polishing time to obtain an amount of cumulative change in the spectrum; and monitoring progress of polishing of the substrate based on the amount of cumulative change in the spectrum.

Still another aspect of the present invention is to provide a polishing monitoring apparatus including: a light-applying unit configured to direct light to the substrate during polishing of the substrate; a light-receiving unit configured to receive reflected light from the substrate; a spectroscope configured to measure intensity of the reflected light at each wavelength; and a processing device configured to process measurement data from the spectroscope, wherein the processing device is configured to produce spectrum indicating relationship between intensity and wavelength from measured values of the intensity, calculate an amount of change in the spectrum per predetermined time, integrate the amount of change in the spectrum with respect to polishing time to obtain an amount of cumulative change in the spectrum, and monitor the progress of polishing of the substrate based on the amount of cumulative change in the spectrum.

Still another aspect of the present invention is to provide a program for enabling a computer to execute the steps of: producing spectrum indicating relationship between intensity and wavelength of reflected light from a substrate; calculating an amount of change in the spectrum per predetermined time; integrating the amount of change in the spectrum with respect to polishing time to obtain an amount of cumulative change in the spectrum; and monitoring progress of polishing of the substrate based on the amount of cumulative change in the spectrum.

Because the progress of polishing is monitored based on the amount of change in the spectrum in its entirety, the present invention can be applied to polishing of various substrates. In particular, even in the case where the wavelengths of the local extremum points of the spectrum do not change greatly because of a small amount of polishing and because of multilayer transparent films having greatly different refractive indexes (e.g., like a polishing process for adjusting the height of copper interconnects), the method according to the present invention can accurately obtain the change in thickness of a film to be polished. Because the amount of cumulative change in the spectrum, which is obtained by integrating (or adding up) the amount of change in the spectrum, corresponds to the amount of polishing (i.e., the amount of film removed or the change in film thickness), the polishing end point can be detected accurately without being affected by the variation in thickness of the underlying film between substrates. Moreover, even if the substrate has a complicated multilayer structure, the amount of cumulative change in the spectrum increases monotonically during polishing, basically. Therefore, it is easy to grasp the progress of substrate polishing from the amount of cumulative change in the spectrum. That is, by simply comparing the amount of cumulative change in the spectrum with a predetermined target value or threshold value, the polishing end point can be detected easily.

DETAILED DESCRIPTION OF THE INVENTION

Figure 1:
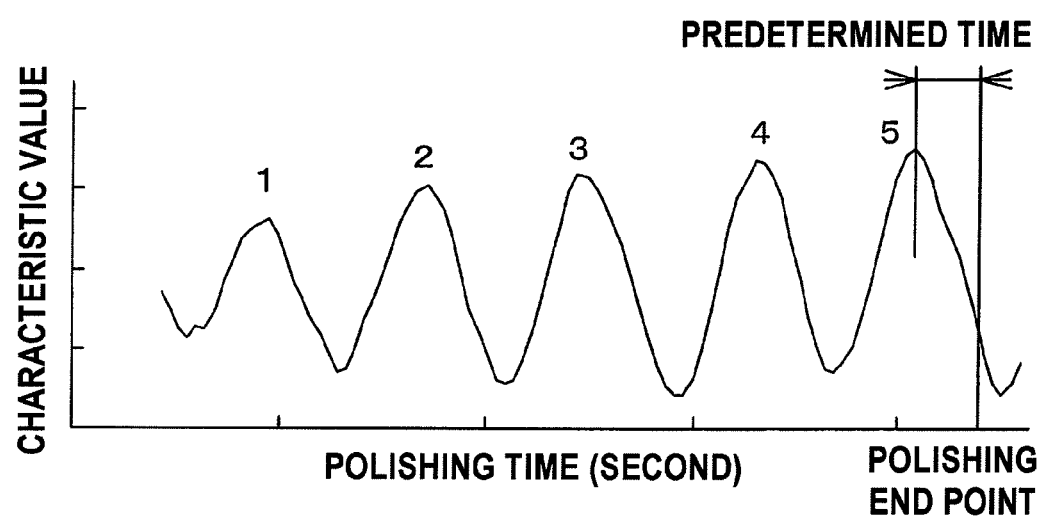
FIG. 1 is a graph showing a manner of change in characteristic value with polishing time.
Figure 2A:
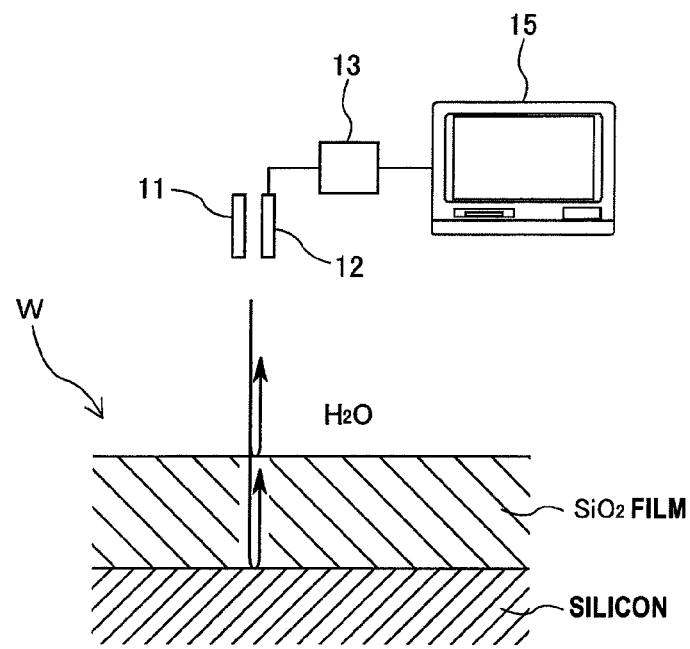
FIG. 2A is a schematic view illustrating the principle of a polishing monitoring method according to an embodiment of the present invention.
Figure 2B:
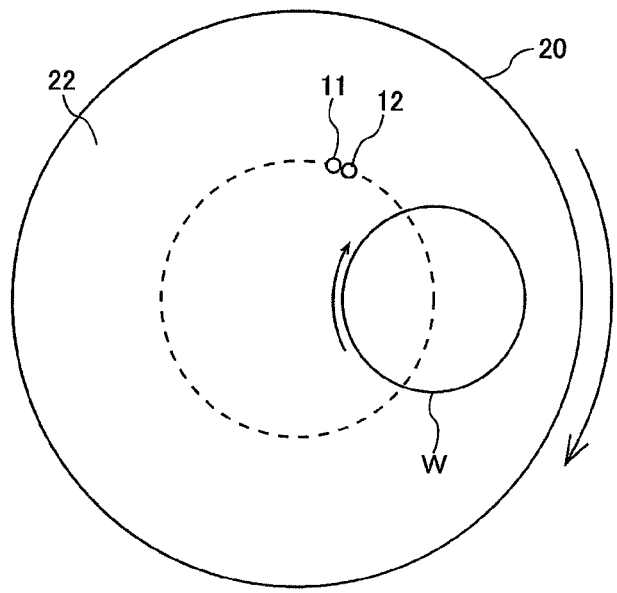
FIG. 2B is a plan view showing positional relationship between a substrate and a polishing table.

Embodiments of the present invention will be described below with reference to the drawings. FIG. 2A is a schematic view showing the principle of a polishing monitoring method according to an embodiment of the present invention, and FIG. 2B is a plan view showing a positional relationship between a substrate and a polishing table. As shown in FIG. 2A, a substrate W, to be polished, has an underlying layer (e.g., a silicon layer) and a film (e.g., a dielectric film, such as $SiO_2$, having a light permeability) formed on the underlying layer. The substrate W is held by a top ring (not shown in FIG. 2A and FIG. 2B) and is rotated about its center as indicated by arrow. A surface of the substrate W is pressed by the top ring against a polishing pad 22 on a rotating polishing table 20. The film of the substrate W is thus polished by sliding contact with the polishing pad 22.

A light-applying unit 11 and a light-receiving unit 12 are arranged so as to face the surface of the substrate W. The light-applying unit 11 is configured to emit light in a direction substantially perpendicular to the surface of the substrate W, and the light-receiving unit 12 is configured to receive the reflected light from the substrate W. The light emitted by the light-applying unit 11 is multiwavelength light. As shown in FIG. 2B, the light is applied to regions including the center of the substrate W each time the polishing table 20 makes one revolution. A spectroscope 13 is coupled to the light-receiving unit 12. This spectroscope 13 decomposes the reflected light according to wavelength and measures the intensity of the reflected light at each wavelength.

A processing device 15 is coupled to the spectroscope 13. This processing device 15 is configured to read measurement data obtained by the spectroscope 13 and produce intensity distribution of the reflected light from the measured values of the intensity. More specifically, the processing device 15 produces a spectrum which indicates the light intensity at each of the wavelengths. This spectrum is expressed as a line graph indicating a relationship between wavelength and intensity of the reflected light. The processing device 15 is further configured to monitor the progress of polishing from a change in the spectrum and determine a polishing end point. A general-purpose computer or a dedicated computer can be used as the processing device 15. The processing device 15 performs predetermined processing steps according to a program (or computer software).

Figure 3:
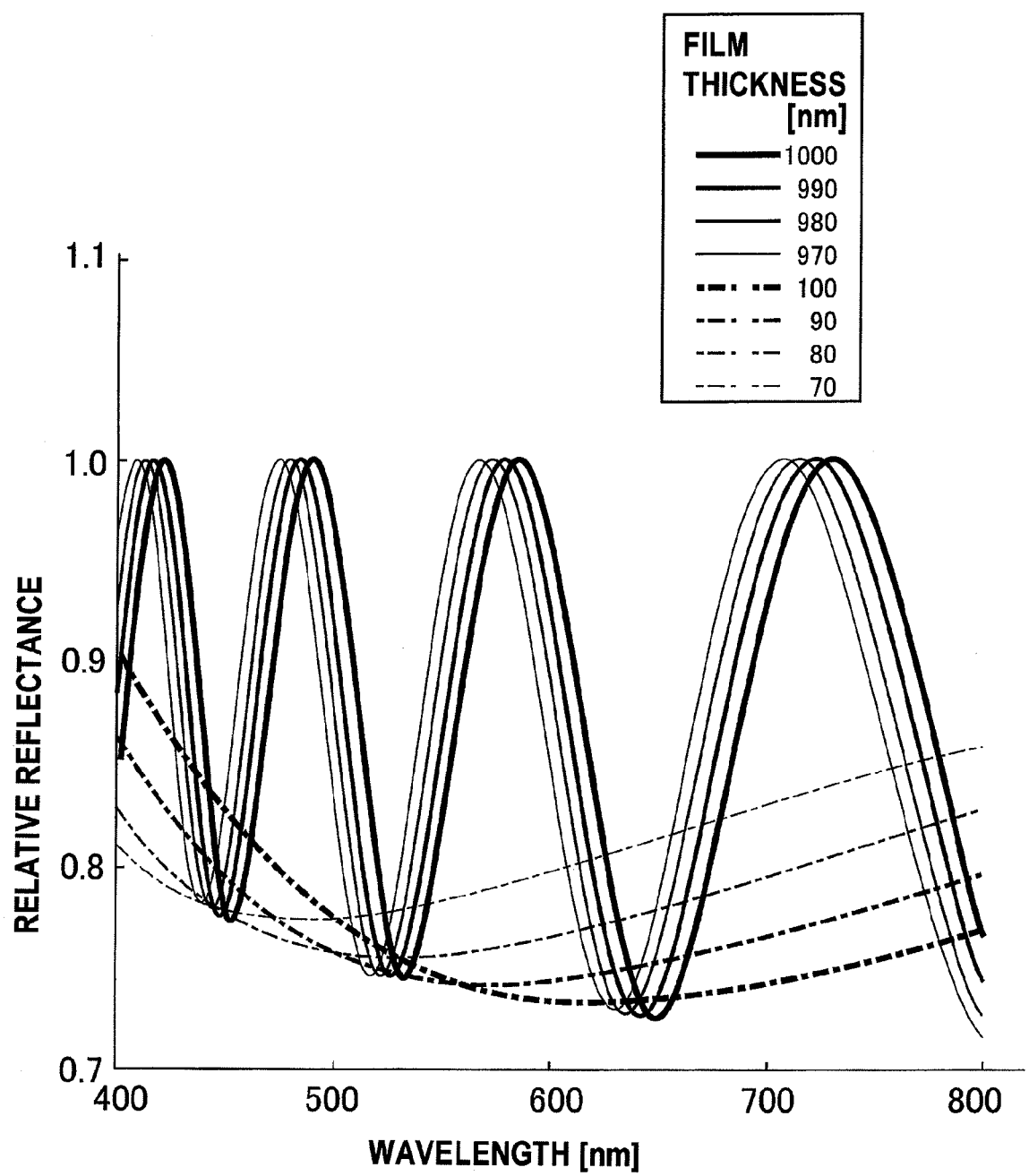
FIG. 3 is a graph showing spectra of reflected light obtained by simulation performed based on the theory of interference of light.

FIG. 3 is a graph showing spectra of the reflected light obtained by polishing simulation performed on a substrate having the structure shown in FIG. 2A based on the theory of interference of light. In FIG. 3, a horizontal axis represents wavelength of light, and a vertical axis represents relative reflectance derived from the intensity of the light. The relative reflectance is an index that indicates the intensity of light. More specifically, the relative reflectance is a ratio of the intensity of the reflected light to a predetermined reference intensity. By dividing the intensity of the reflected light (i.e., the actually measured intensity) by the predetermined reference intensity, noise components are removed and therefore intensity of the light with no noise can be obtained. The predetermined reference intensity may be an intensity of the reflected light obtained when polishing a silicon wafer with no film thereon in the presence of water. In the case of polishing simulation, the relative reflectance is determined by simply dividing the intensity of the reflected light from the substrate obtained with respect to each wavelength (in the simulation, a reflectance indicating a ratio of the intensity of the reflected light to the intensity of the incident light) by the reference intensity (in the simulation, a reflectance indicating a ratio of the intensity of the reflected light to the intensity of the incident light). In the case of actual polishing, before conducting the aforementioned division, a dark level (which is a background intensity obtained under the condition that the light is cut off) is subtracted from both dividend and divisor. Instead of using the relative reflectance, it is possible to use the intensity of the light as it is.

In the actual polishing, the relative reflectance $R(\lambda)$ can be calculated by using $$R(\lambda) = \frac{E(\lambda) - D(\lambda)}{B(\lambda) - D(\lambda)} \quad (1)$$

where $\lambda$ is wavelength, $E(\lambda)$ is the intensity of the reflected light from the substrate, $B(\lambda)$ is the reference intensity, and $D(\lambda)$ is the background intensity (i.e., dark level) obtained under condition that the substrate does not exist.

The simulation of the reflected light from the substrate based on the theory of interference of light was conducted under a condition that water ($H_2O$) is used as a medium of the light. The graph in FIG. 3 shows plural spectra that were obtained at film-thickness intervals of 10 nm. As shown in FIG. 3, when the film thickness is large, intervals of the local maximum points and the local minimum points (which will be correctively referred to as local extremum points) of the spectrum are short and the number of local extremum points is large. On the other hand, when the film thickness is small, the number of local extremum points is small and the spectrum describes a gentle curve. Further, as the film thickness decreases (i.e., as polishing progresses), the spectrum moves to shorter wavelengths (in FIG. 3, the spectrum moves to the left).

Figure 4:
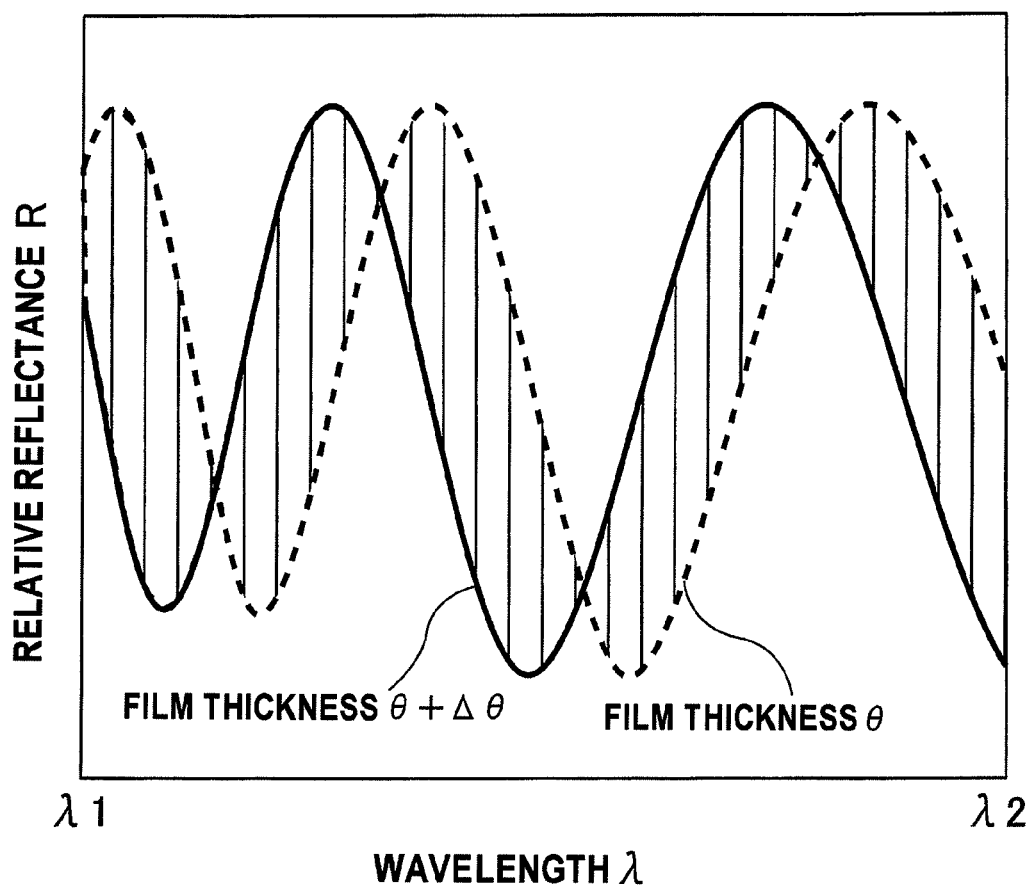
FIG. 4 is a graph showing adjacent two of the spectra shown in FIG. 3.

FIG. 4 is a schematic diagram showing two spectra corresponding to a film-thickness difference $\Delta\theta$, with respect to spectra as shown in FIG. 3. The symbol $\theta$ represents film thickness. Since the film thickness $\theta$ decreases with time during polishing, the film-thickness difference $\Delta\theta$ is smaller than zero (i.e., $\Delta\theta<0$). As described above, the spectrum moves along the wavelength axis with the change in the film thickness. As shown in FIG. 4, an amount of change in the spectrum corresponding to the film-thickness difference $\Delta\theta$ corresponds to a region (indicated by hatching) surrounded by the above-described two spectra obtained at two different points of time. As can be seen from FIG. 3, an area of this region is approximately constant regardless of whether the film thickness is large or small, so long as the film-thickness difference $\Delta\theta$ is small sufficiently (in this example, $\Delta\theta=-10$ nm). Therefore, it is expected to be able to grasp the change in the film thickness by integrating (i.e., adding up) the above-described area or variate similar thereto during polishing.

Thus, in this method, the amount of change in the spectrum $V(t)$ is expressed by $$V(t) = \sqrt{1/N_\lambda * \sum_{\lambda=\lambda 1}^{\lambda 2} [R(\lambda, t+\Delta t) - R(\lambda, t)]^2} \quad (2)$$

wherein $\lambda$ is wavelength of the light, $\lambda 1$, $\lambda 2$ are minimum wavelength and maximum wavelength that determine a wavelength range of the spectrum to be monitored, $N_\lambda$ is the number of wavelengths in the wavelength range, t is time (polishing time), $\Delta t$ is a predetermined time interval (or time increment or time pitch), and $R(\lambda, t)$ is relative reflectance at a wavelength $\lambda$ and a time t. As an example, $\Delta t$ may be a time required for the polishing table to make p-revolutions ("p" is a small natural number).

The amount of change in the spectrum $V(t)$ may be expressed as an amount of change in the spectrum per unit time, i.e., a rate of change in the spectrum. The rate of change in the spectrum $V(t)$ is expressed as $$V(t) = 1/\Delta t * \sqrt{1/N_\lambda * \sum_{\lambda=\lambda 1}^{\lambda 2} [R(\lambda, t+\Delta t) - R(\lambda, t)]^2} \quad (3)$$

The amount of change in the spectrum per predetermined time $\Delta t$ is expressed as a magnitude of relative change between two spectra in the aforementioned wavelength range (i.e., a magnitude of displacement). The above-described equation (2) is an equation that expresses the amount of change in the spectrum as root mean square. More specifically, the amount of change in the spectrum $V(t)$ given by the equation (2) is root mean square of difference in light intensity between two spectra at each wavelength.

Further, from the equation (2) and the equation (3), a cumulative value $A(t)$ of the amount of change in the spectrum along the temporal axis is given by $$A(t) = \sum_{t=t_o}^{t} V(t) \quad (4)$$

or $$A(t) = \sum_{t=t_o}^{t} V(t)\Delta t \quad (5)$$

where $t_0$ is a time when monitoring of the change in film thickness is started. The right-hand sides of the equation (4) and the equation (5) may be multiplied by an appropriate factor so that the value of A(t) is adjusted to be large enough for observation.

The value of $\Delta t$ in the equation (5) may not necessarily be equal to the value of $\Delta t$ in the equation (3). For example, $\Delta t$ in the equation (3) and $\Delta t$ in the equation (5) may be set as follows:

(Step i) The relative reflectance R(t) is measured every second.

(Step ii) $\Delta t$ in the equation (3) is set to two seconds, so that the rate of change in the spectrum V(t) is calculated every second from the amount of change in the spectrum between points of time which are separated by two seconds.

(Step iii) $\Delta t$ in the equation (5) is set to one second, so that the amount of cumulative change in the spectrum A(t) is calculated every second.

The method of formulating the amount of change in the spectrum is not limited to the above-described equations, and other method can be used. For example, the amount of change in the spectrum V(t) may be mean square of difference in light intensity between two spectra at each wavelength. The wavelength range of the spectrum to be monitored may be plural discontinuous ranges. Furthermore, the amount of change in the spectrum V(t) may be defined as a value that corresponds to an area of the hatched region shown in FIG. 4, which is given by $$V(t) = \Delta\lambda * \sum_{\lambda=\lambda 1}^{\lambda 2} |R(\lambda, t+\Delta t) - R(\lambda, t)| \quad (6)$$

wherein $\Delta\lambda$ is wavelength interval.

Like the equation (2), the amount of change in the spectrum V(t) may be expressed as an average of absolute values of difference in the relative reflectance with respect to individual wavelengths in the wavelength range [$\lambda 1, \lambda 2$] of the spectrum to be monitored. This average of absolute values is given by $$V(t) = 1/N_\lambda * \sum_{\lambda=\lambda 1}^{\lambda 2} |R(\lambda, t+\Delta t) - R(\lambda, t)| \quad (7)$$

Further, normalized relative reflectance $R_N(\lambda, t)$ may be used instead of $R(\lambda, t)$ in the equations (2), (3), and (7). This normalized relative reflectance $R_N(\lambda, t)$ is given by dividing the relative reflectance $R(\lambda, t)$ by an average of the relative reflectance in a predetermined wavelength range. The above-described range [$\lambda 1, \lambda 2$] may be used as the predetermined wavelength range in the normalization. The following equation (8) is used for calculating the normalized relative reflectance $R_N(\lambda, t)$.

$$R_N(\lambda, t) = R(\lambda, t) \Big/ \left[ 1/N_\lambda * \sum_{\lambda=\lambda 1}^{\lambda 2} R(\lambda, t) \right] \quad (8)$$

The following equations (9) and (10) are equations obtained by replacing $R(\lambda, t)$ in the equations (2) and (7) with $R_N(\lambda, t)$ in the equation (8), respectively.

$$V(t) = \sqrt{1/N_\lambda * \sum_{\lambda=\lambda 1}^{\lambda 2} [R_N(\lambda, t+\Delta t) - R_N(\lambda, t)]^2} \quad (9)$$

$$V(t) = 1/N_\lambda * \sum_{\lambda=\lambda 1}^{\lambda 2} |R_N(\lambda, t+\Delta t) - R_N(\lambda, t)| \quad (10)$$

Use of the normalized relative reflectance can remove an influence of a change in quantity of light. For example, as the polishing pad wears, a distance between the substrate and the optical sensor (i.e., the light-applying unit 11 and the light-receiving unit 12) changes, thus causing the change in quantity of light received. Even in such a case, by using the normalized relative reflectance, it is possible to eliminate the influence of the change in quantity of light. Therefore, the amount of change in the spectrum can be calculated without being affected by the change in quantity of light.

Figure 5A:
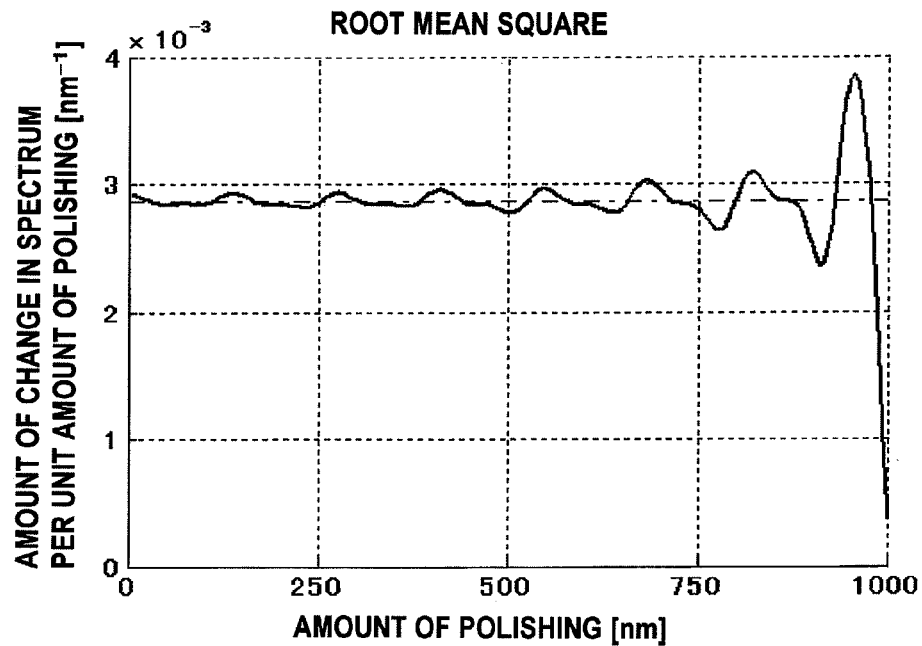
FIG. 5A is a graph showing a simulation result of polishing of the substrate shown in FIG. 2A.
Figure 5B:
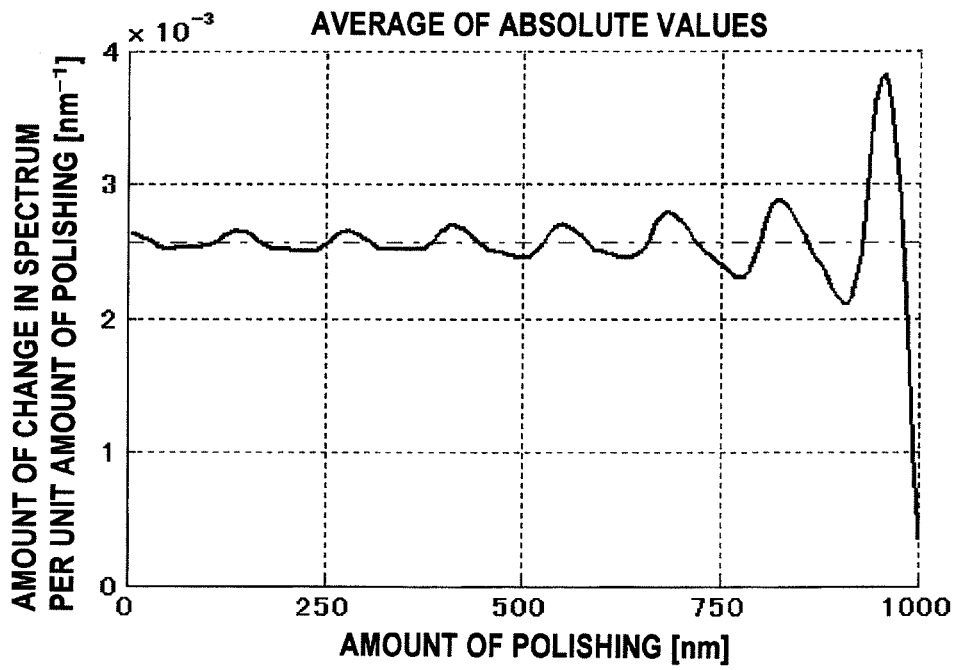
FIG. 5B is a graph showing a simulation result of polishing of the substrate shown in FIG. 2A.
Figure 5C:
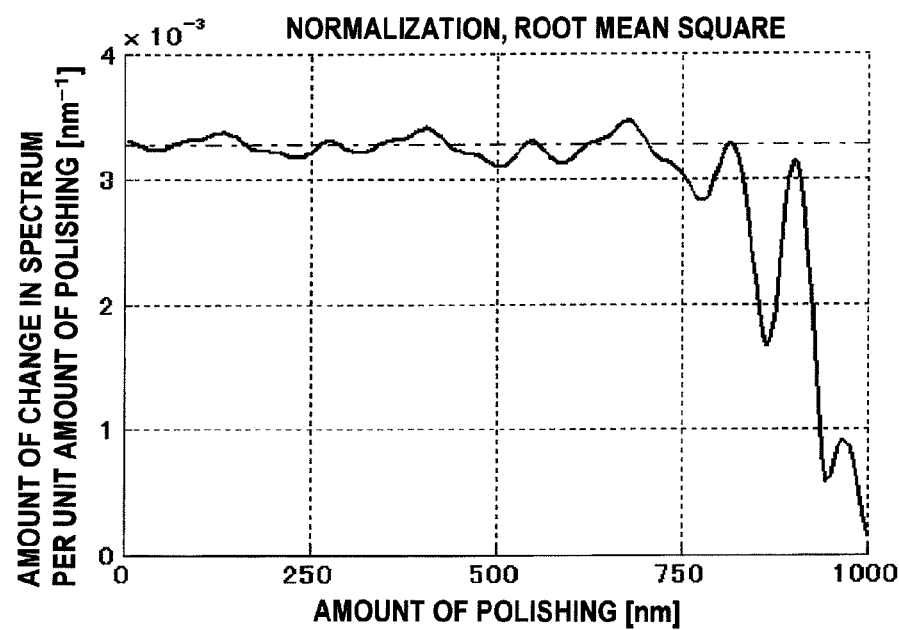
FIG. 5C is a graph showing a simulation result of polishing of the substrate shown in FIG. 2A.
Figure 5D:
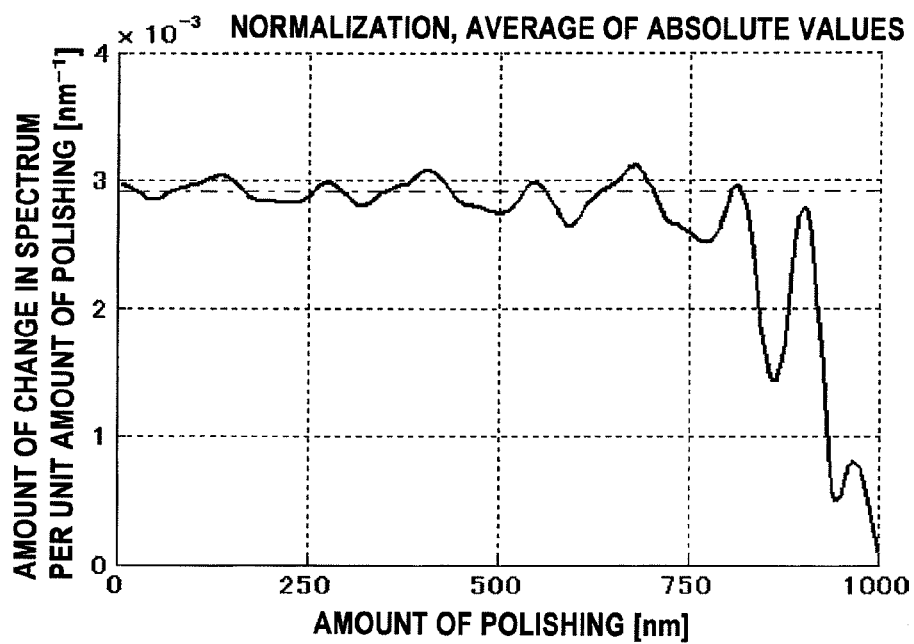
FIG. 5D is a graph showing a simulation result of polishing of the substrate shown in FIG. 2A.

FIG. 5A through FIG. 5D are graphs each showing a simulation result of polishing of the substrate having an oxide film with an initial thickness of 1000 nm as shown in FIG. 2A. FIG. 5A corresponds to the equation (2), FIG. 5B corresponds to the equation (7), FIG. 5C corresponds to the equation (9), and FIG. 5D corresponds to the equation (10).

Under a condition that a polishing rate is constant, the film thickness $\theta$ varies by $\Delta\theta$ (<0) while the time t increases by $\Delta t$. Therefore, the time $\Delta t$ corresponds to the film thickness difference $\Delta\theta$. Using $\theta$ and $\Delta\theta$ instead of t and $\Delta t$, the equation (2) and the equation (3) can be written as follows.

$$V(\theta) = \sqrt{1/N_\lambda * \sum_{\lambda=\lambda 1}^{\lambda 2} [R(\lambda, \theta+\Delta\theta) - R(\lambda, \theta)]^2} \quad (11)$$

$$V(\theta) = -1/\Delta\theta * \sqrt{1/N_\lambda * \sum_{\lambda=\lambda 1}^{\lambda 2} [R(\lambda, \theta+\Delta\theta) - R(\lambda, \theta)]^2} \quad (12)$$

Further, the equation (4) and the equation (5) are written as follows.

$$A(\theta) = \sum_{\theta=\theta_o}^{\theta} V(\theta) \quad (13)$$

$$A(\theta) = -\sum_{\theta=\theta_o}^{\theta} V(\theta)\Delta\theta \quad (14)$$

Although $\theta$ is typically smaller than an initial thickness $\theta_0$ (i.e., $\theta < \theta_0$), the symbol $\Sigma$ in the equation (13) and the equation (14) represents summation of $V(\theta)$ in the range of $\theta$ to $\theta_0$.

The above-described equation (7) can be expressed as $$V(\theta) = 1/N_\lambda * \sum_{\lambda=\lambda_1}^{\lambda_2} |R(\lambda, \theta + \Delta\theta) - R(\lambda, \theta)| \quad (15)$$

Further, the equation (9) and the equation (10) can be expressed as $$V(\theta) = \sqrt{1/N_\lambda * \sum_{\lambda=\lambda_1}^{\lambda_2} [R_N(\lambda, \theta + \Delta\theta) - R_N(\lambda, \theta)]^2} \quad (16)$$

$$V(\theta) = 1/N_\lambda * \sum_{\lambda=\lambda_1}^{\lambda_2} |R_N(\lambda, \theta + \Delta\theta) - R_N(\lambda, \theta)| \quad (17)$$

In FIG. 5A through FIG. 5D, vertical axis represents the amount of change in the spectrum per unit amount of polishing which is 1 nm, and a horizontal axis represents the amount of polishing, i.e., the amount of film removed. It can be seen from the graphs in FIG. 5A through FIG. 5D that the amount of change in the spectrum is approximately constant when the film thickness is large although there are slight periodic fluctuations and that an amplitude of the fluctuation increases gradually as the film thickness decreases.

Figure 6A:
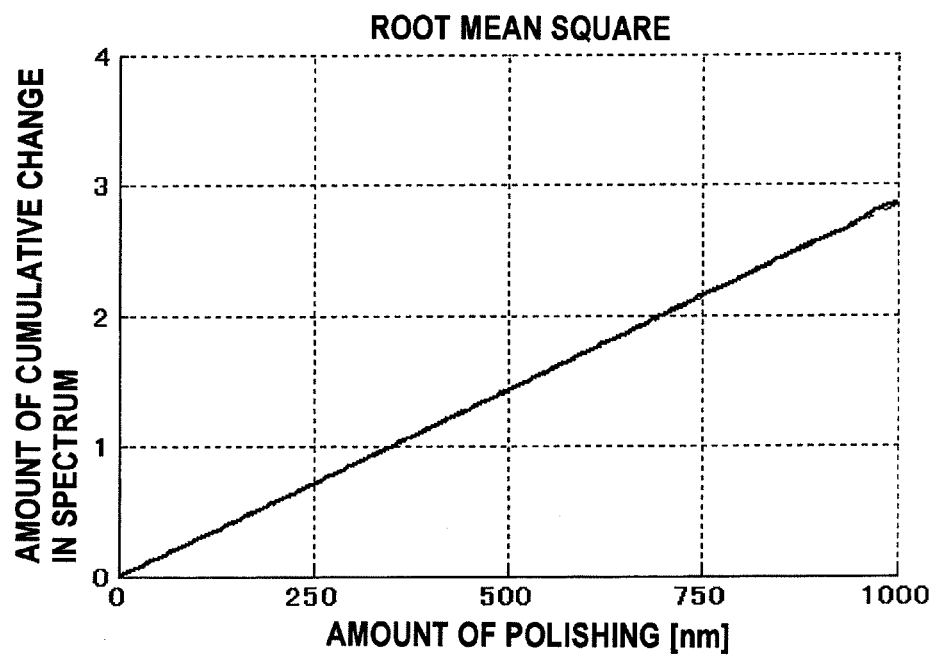
FIG. 6A is a graph showing an amount of cumulative change in the spectrum $A(\theta)$.
Figure 6B:
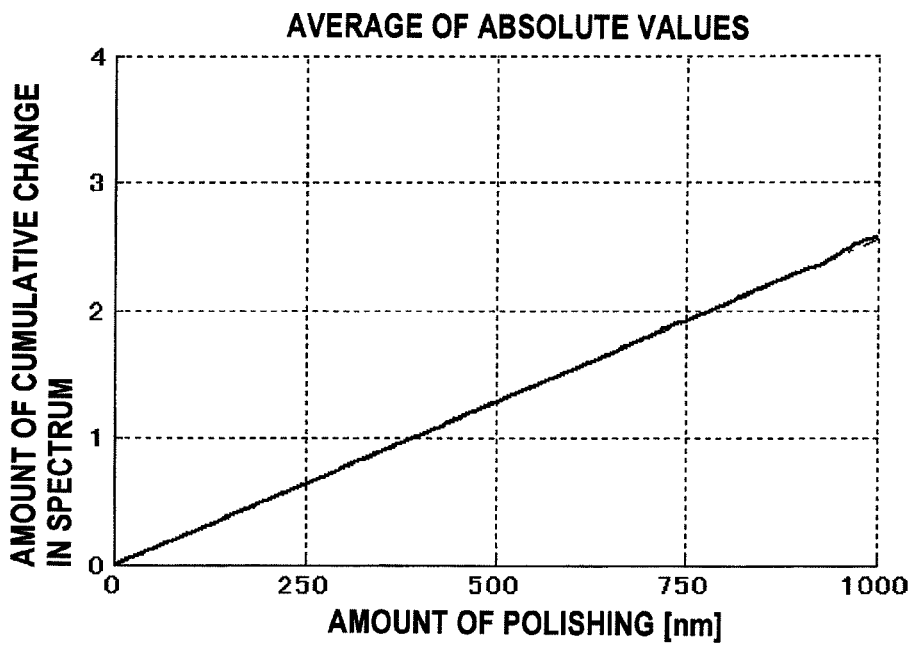
FIG. 6B is a graph showing an amount of cumulative change in the spectrum $A(\theta)$.
Figure 6C:
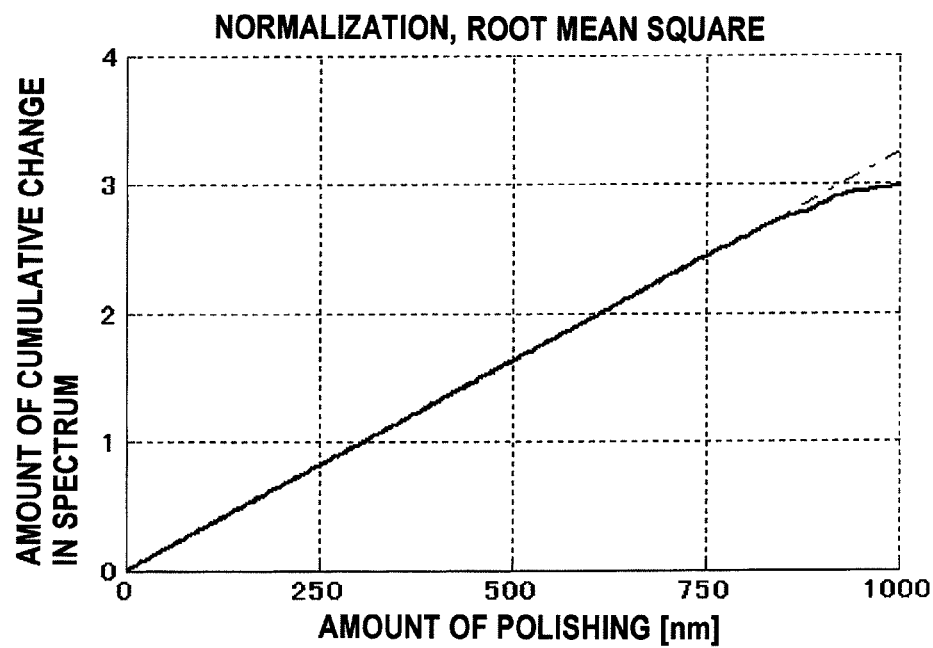
FIG. 6C is a graph showing an amount of cumulative change in the spectrum $A(\theta)$.
Figure 6D:
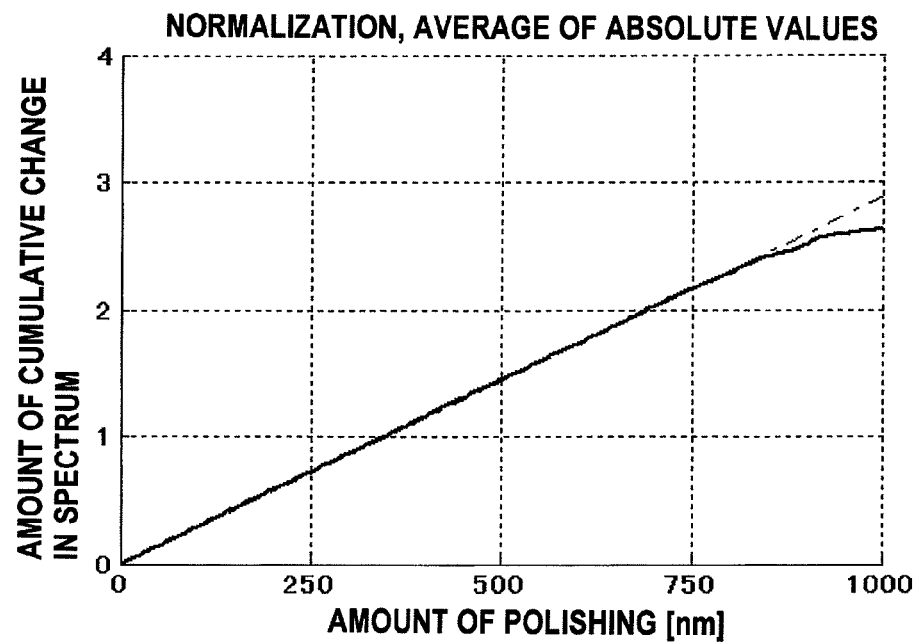
FIG. 6D is a graph showing an amount of cumulative change in the spectrum $A(\theta)$.

FIG. 6A through FIG. 6D are graphs each showing the amount of cumulative change in the spectrum $A(\theta)$ calculated using the equation (13). More specifically, FIG. 6A is a graph obtained from the equation (11) and the equation (13), FIG. 6B is a graph obtained from the equation (15) and the equation (13), FIG. 6C is a graph obtained from the equation (16) and the equation (13), and FIG. 6D is a graph obtained from the equation (17) and the equation (13).

As described above, because the amount of change in the spectrum fluctuates periodically, an error from an average level due to the fluctuation hardly accumulates. Therefore, as shown in FIG. 6A through FIG. 6D, the amount of cumulative change in the spectrum $A(\theta)$ increases approximately linearly until the amount of polishing reaches in the range of 800 nm to 900 nm (i.e., until the film thickness reaches in the range of 200 nm to 100 nm). It can be seen from these results that the decrease in the film thickness (i.e., the amount of film removed) can be grasped from the amount of cumulative change in the spectrum. The above-described processing device 15 calculates the amount of cumulative change in the spectrum during polishing of the substrate and monitors the progress of substrate polishing from the amount of cumulative change in the spectrum. Further, the processing device 15 determines the polishing end point from the amount of cumulative change in the spectrum. The polishing end point can be a point of time when the amount of cumulative change in the spectrum has reaches a predetermined target value.

FIG. 7A through FIG. 7D show simulation results of studying how much the amount of polishing, which is estimated from the amount of cumulative change in the spectrum, has an error from a true amount of polishing at each point of time during polishing when polishing the oxide film of the substrate shown in FIG. 2A by 500 nm from an initial thickness of 1000 nm.

At a polishing start point (the amount of polishing is 0 nm, the film thickness is 1000 nm), both the amount of cumulative change in the spectrum and the amount of polishing are zero. Therefore, assuming that an error of an estimated amount of polishing at the polishing end point (the amount of polishing is 500 nm, the film thickness is 500 nm) is zero and that the amount of polishing is perfectly proportional to the amount of cumulative change in the spectrum, the estimated amount of polishing at the film thickness $\theta$ is

[$A(\theta) - A(1000 \text{ nm})$]/[$A(500 \text{ nm}) - A(1000 \text{ nm})$]× 500 nm where $A(1000 \text{ nm})$ is zero.

The true amount of polishing at each point of time during polishing is expressed by 1000 nm$-\theta$. Therefore, an estimated error $E(\theta)$ of the amount of polishing at each point of time during polishing is described as $$E(\theta) = A(\theta)/A(500 \text{ nm}) \times 500 \text{ nm} - (1000 \text{ nm} - \theta) \quad (18)$$

Figure 7A:
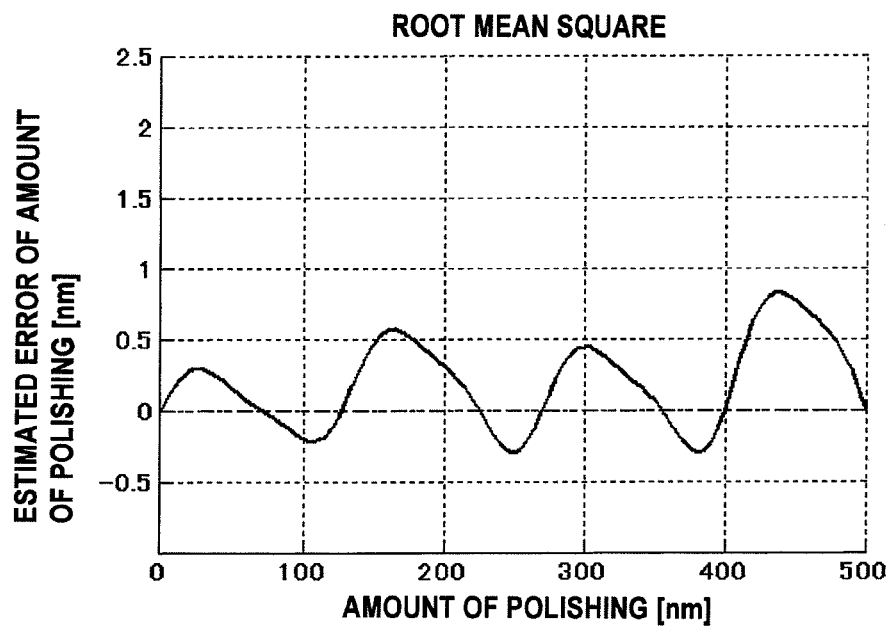
FIG. 7A is a graph showing error of amount of polishing obtained from the simulation result of substrate polishing.
Figure 7B:
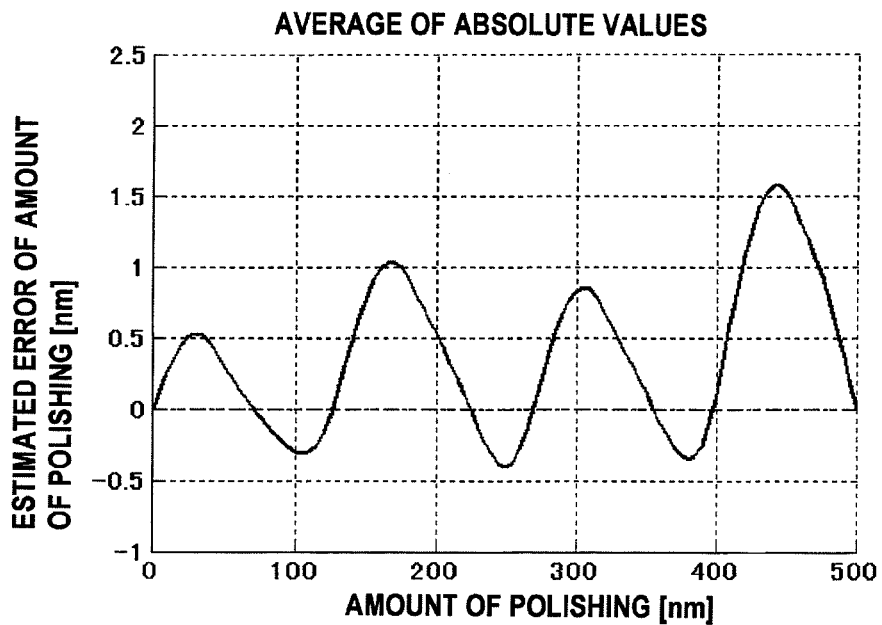
FIG. 7B is a graph showing error of amount of polishing obtained from the simulation result of substrate polishing.
Figure 7C:
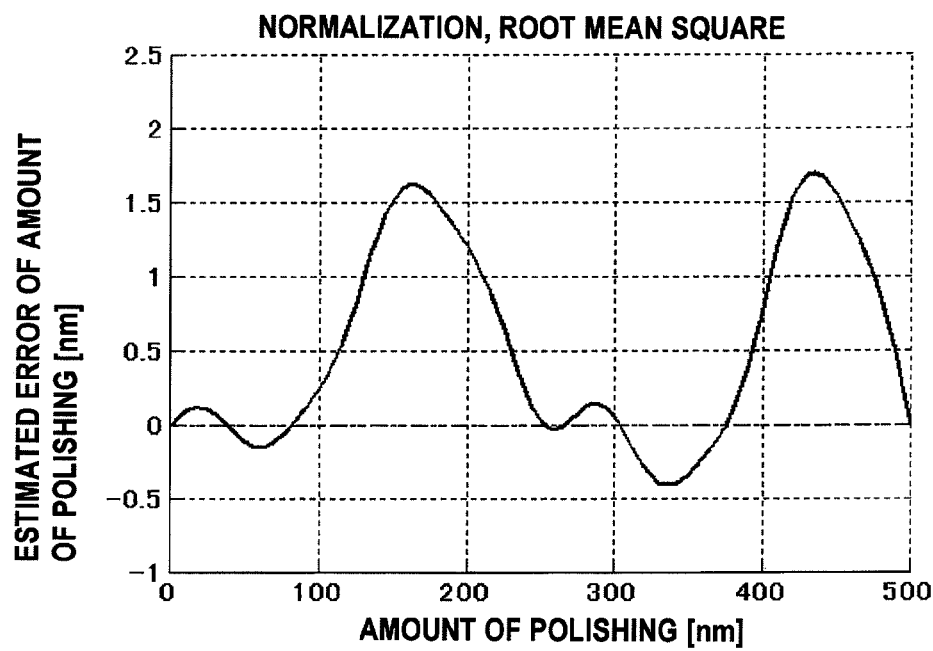
FIG. 7C is a graph showing error of amount of polishing obtained from the simulation result of substrate polishing.
Figure 7D:
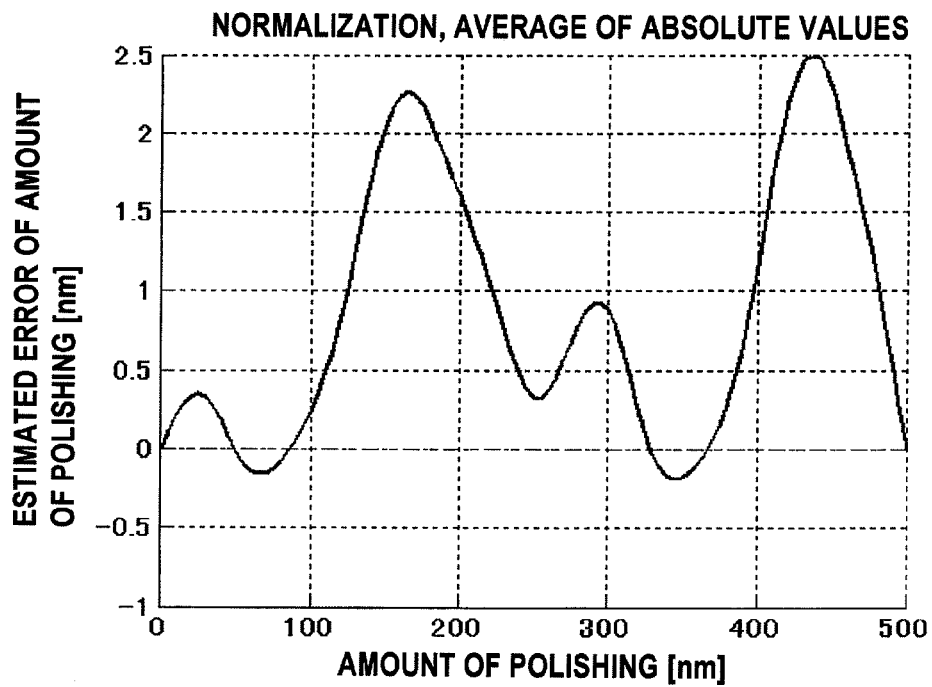
FIG. 7D is a graph showing error of amount of polishing obtained from the simulation result of substrate polishing.

In the graphs of FIG. 7A through FIG. 7D, a horizontal axis represents the amount of polishing, i.e., the amount of film removed, and a vertical axis represents error $E(\theta)$ of the amount of polishing determined from the above-described equation (18) containing the film thickness $\theta$ as variable. More specifically, FIG. 7A is a graph obtained from the equation (11), the equation (13), and the equation (18), FIG. 7B is a graph obtained from the equation (15), the equation (13), and the equation (18), FIG. 7C is a graph obtained from the equation (16), the equation (13), and the equation (18), and FIG. 7D is a graph obtained from the equation (17), the equation (13), and the equation (18).

FIG. 7A shows that the error is approximately in the range of −0.3 nm to 0.8 nm during polishing. It can be seen from this result that the progress of polishing can be monitored accurately based on the amount of cumulative change in the spectrum. Although the error of the amount of polishing in FIG. 7B through FIG. 7D is larger than that in FIG. 7A, values of the error in FIG. 7D, which shows the largest error of the amount of polishing, are as relatively small as less than 2.5 nm. Therefore, by obtaining the relationship between the amount of cumulative change in the spectrum and the amount of polishing in advance, it is possible to estimate the amount of polishing accurately from the amount of cumulative change in the spectrum obtained during polishing of the substrate. The relationship between the amount of cumulative change in the spectrum and the amount of polishing can be obtained by: polishing a reference substrate of the same type as (i.e., identical or similar to) the substrate to be polished to obtain an amount of cumulative change in the reference spectrum; measuring film thickness of the reference substrate before and after polishing thereof (i.e., measuring an initial film thickness and a final film thickness) to determine the amount of polishing from the polishing start to the polishing end; and correlating the amount of cumulative change in the reference spectrum with the amount of polishing, on the assumption that the amount of cumulative change in the reference spectrum is proportional to the amount of polishing during polishing.

When a dielectric film is formed on a film having interconnects (e.g., aluminum) formed therein, a plurality of steps (i.e., concavities and convexities) may be formed on a surface of the dielectric film. If, like this example, large steps exist on the surface of the substrate, the convexities of the substrate surface strongly contacts the polishing pad and are thus polished greatly at the polishing initial stage and on the other hand the concavities are less polished as compared with the convexities, although it depends on the polishing liquid and the polishing pad. Therefore, the surface steps are removed gradually. Consequently, the spectrum does not necessarily change as expected at the initial polishing stage. In such a case, it is preferable to start calculating the amount of cumulative change in the spectrum from a point of time when the surface steps are approximately removed so as to monitor the amount of polishing. The removal point of the surface steps can be determined, for example, by detecting a change in friction between the polishing pad and the substrate based on current of a motor for rotating the polishing table.

Figure 8:
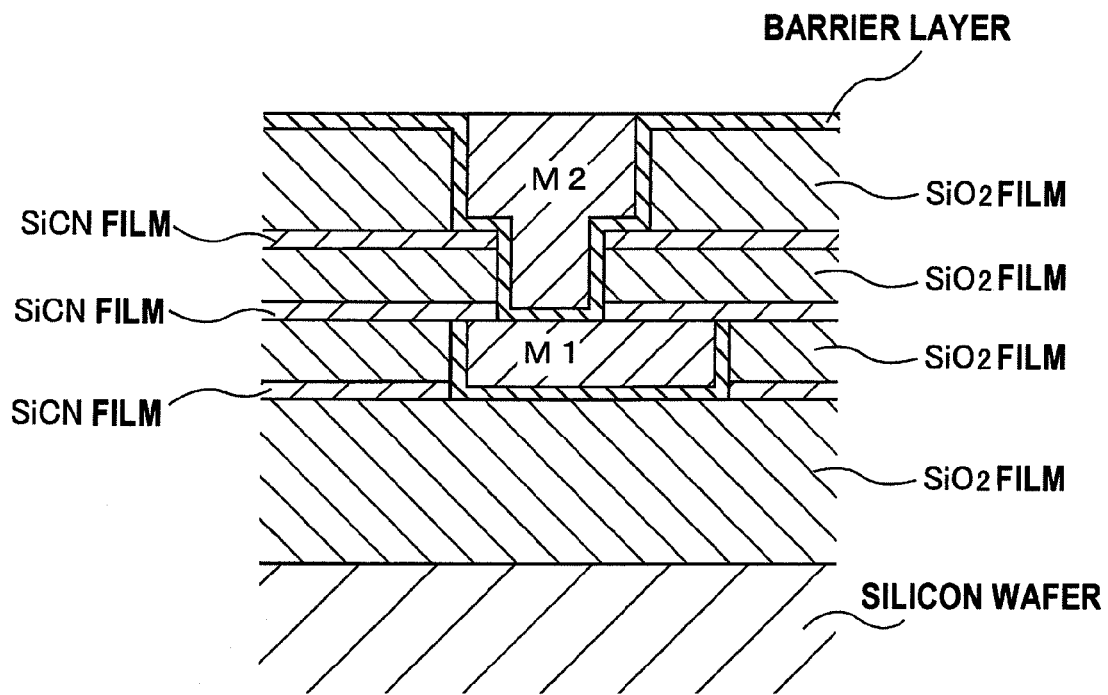
FIG. 8 is a cross-sectional view showing an example of a substrate structure in a Cu interconnect forming process.

FIG. 8 is a cross-sectional view showing an example of a substrate structure in a Cu interconnect forming process. Plural oxide films ($SiO_2$ films) are formed on a silicon wafer. Two-level copper interconnects, i.e., an upper-level copper interconnects M2 and a lower-level copper interconnects M1 which are in electrical communication with each other by via-holes, are formed. SiCN films are formed between the respective oxide films, and a barrier layer (e.g., TaN or Ta) is formed on the uppermost oxide film. Each of the upper three oxide films has a thickness ranging from 100 nm to 200 nm, and each of the SiCN films has a thickness of about 30 nm. The lowermost oxide film has a thickness of about 1000 nm. Structures of the lower layer, such as transistors, are omitted from the drawing. The upper-level copper interconnects M2 are formed in the uppermost oxide film. The uppermost oxide film and the upper-level copper interconnects M2 are polished simultaneously. This polishing process is for the purpose of adjusting a height of the upper-level copper interconnects M2, i.e., interconnect resistance.

Figure 9:
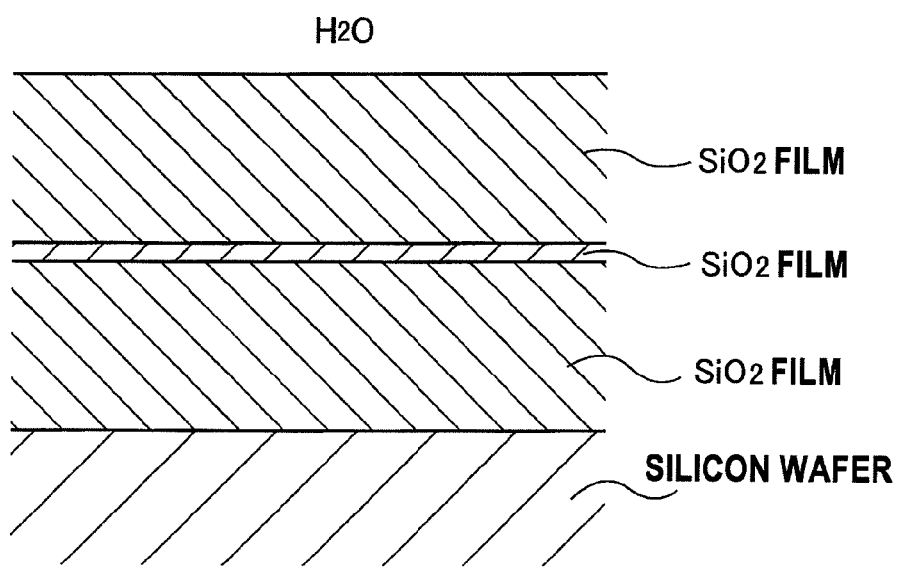
FIG. 9 is a cross-sectional view showing a substrate model for polishing simulation.

The SiCN film is an etching stop layer for stopping etching in a previous process for forming Cu interconnect trenches. SiN may be used instead of SiCN. To examine the influence of the etching stop layer, a substrate model having a simple structure as shown in FIG. 9 was prepared for polishing simulation. In this substrate, a lower $SiO_2$ film is formed on a silicon wafer, a SiCN film serving as the etching stop layer is formed on the lower $SiO_2$ film, and an upper $SiO_2$ film is formed on the SiCN film. The upper $SiO_2$ film has an initial thickness of 200 nm, the SiCN film has a thickness of 30 nm, and the lower $SiO_2$ film has a thickness of 500 nm.

Figure 10:
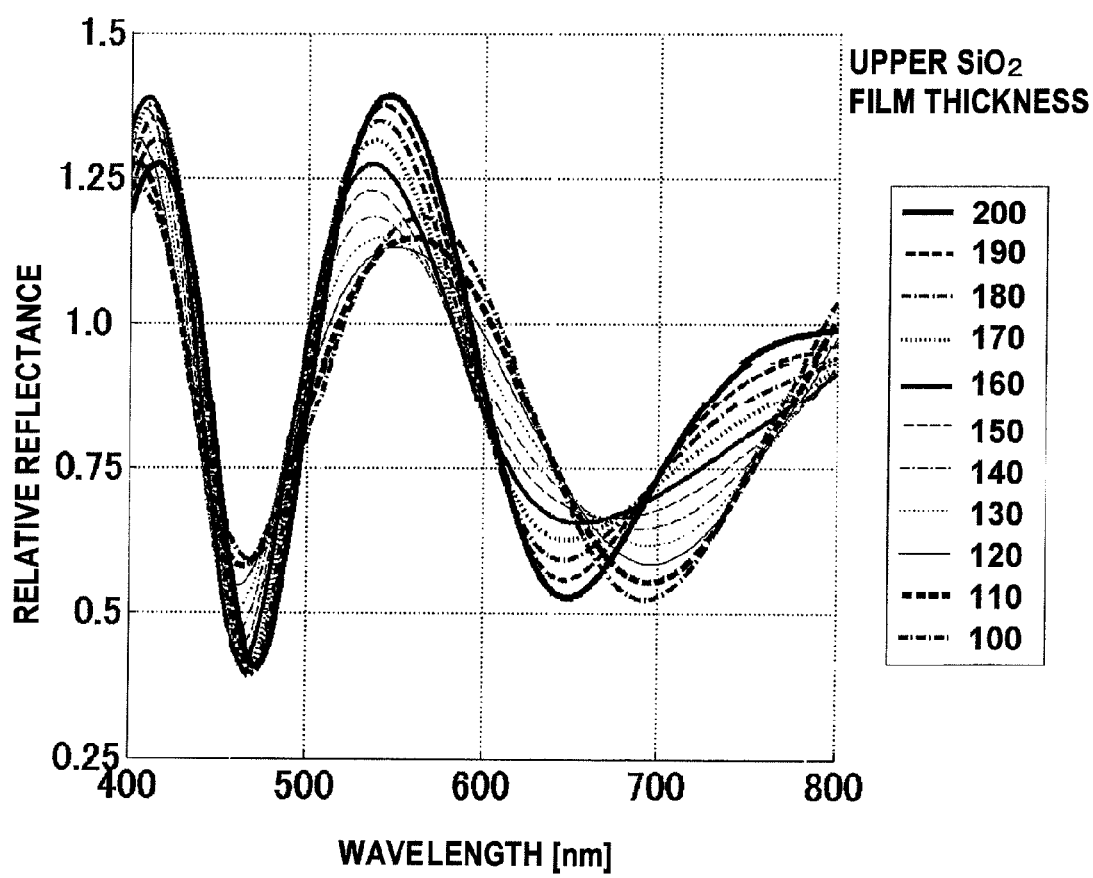
FIG. 10 is a graph showing a change in the spectrum obtained from the simulation result of polishing of an upper $SiO_2$ film, shown in FIG. 9, by 100 nm.
Figure 11:
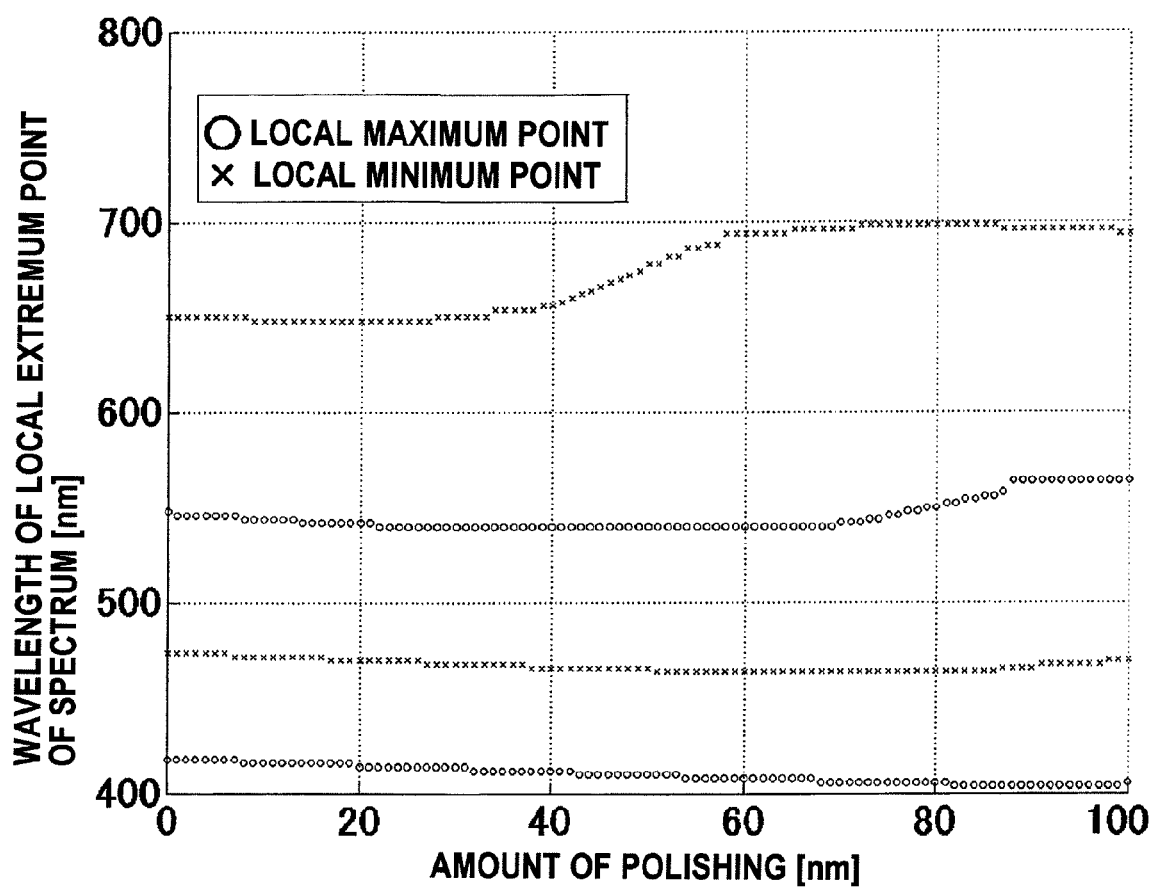
FIG. 11 is a graph showing a change in wavelength of local maximum points and local minimum points of the spectrum shown in FIG. 10.

The polishing simulation was conducted under the condition that water ($H_2O$) was used as the medium of the light. FIG. 10 and FIG. 11 show the simulation results. FIG. 10 is a graph showing a change in the spectrum obtained from the simulation of polishing the upper $SiO_2$ film, shown in FIG. 9, by 100 nm, and FIG. 11 is a graph showing a change in wavelength of local maximum points and local minimum points (i.e., local extremum points) of the spectrum shown in FIG. 10. Unlike the case where a single $SiO_2$ film as shown in FIG. 2A is polished, the wavelengths of the local maximum points and the local minimum points do not vary greatly and the spectrum does not move simply to shorter wavelengths with the decrease in the film thickness. This is because a difference between the refractive index of $SiO_2$ (about 1.46) and the refractive index of SiNC (about 1.83) is larger than a difference between the refractive index of $SiO_2$ and the refractive index of $H_2O$ (about 1.33). In general, when the difference in refractive index between two materials is small, the reflected light from an interface between the materials is weak. As an extreme example, if there is no difference in refractive index on the interface, the reflection does not occur. Therefore, light components reflected from the interface between the SiCN film and the upper $SiO_2$ film or the interface between the SiCN film and the lower $SiO_2$ film through the upper $SiO_2$ film account for a large part of the spectrum of the entire reflected light measured, compared with light components reflected from a top surface of the upper $SiO_2$ film which is the object to be polished. As a result, the number of local extremum points and the wavelength are greatly affected by the lower layers, mainly by the lower $SiO_2$ film, rather than by the SiCN film. Since the lower $SiO_2$ film is not polished, the spectrum obtained during polishing is unlikely to reflect the decrease in thickness of the upper $SiO_2$ film.

Therefore, as shown in FIG. 11, the wavelengths of the local extremum points do not vary while the amount of polishing varies. This makes it difficult to grasp the progress of polishing based on the variation in the wavelength of the local extremum points. However, even in such a case, the spectrum varies with the variation in the amount of polishing (i.e., the film thickness), as shown in FIG. 10.

Figure 12:
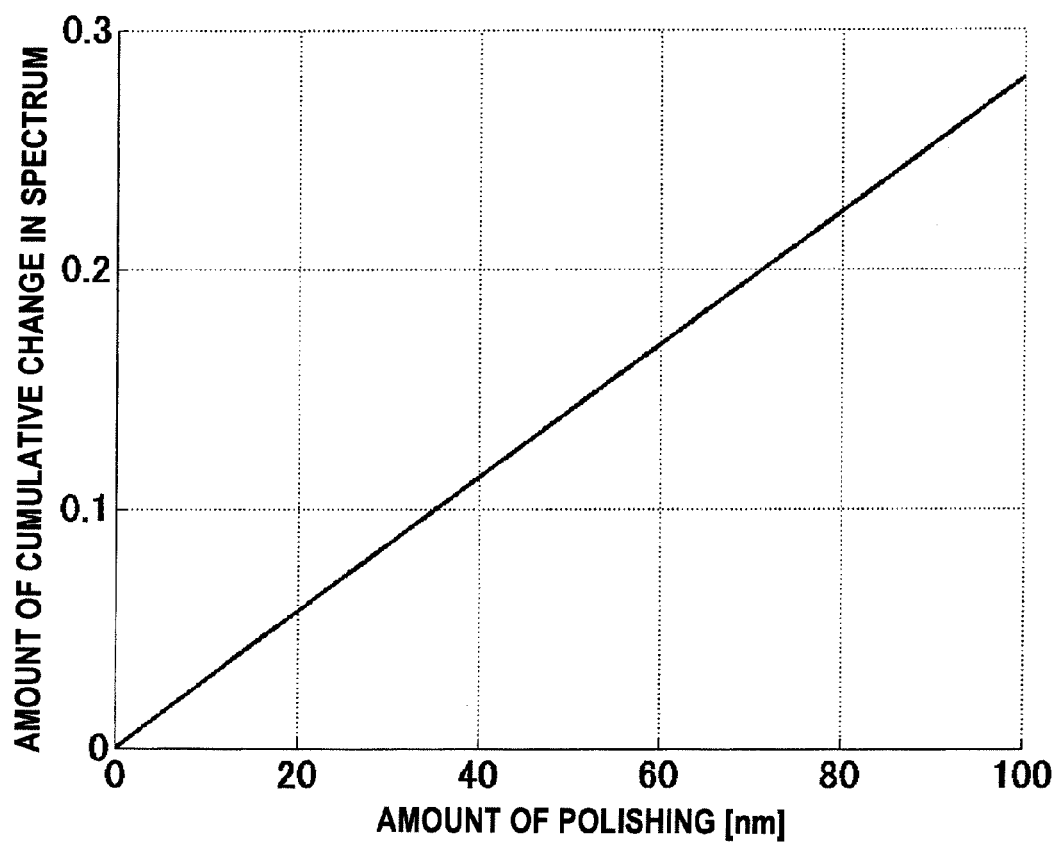
FIG. 12 is a graph showing a variation in the amount of cumulative change in spectrum calculated from the change in the spectrum shown in FIG. 10.

FIG. 12 is a graph showing a change in the amount of cumulative change in the spectrum calculated from the change in the spectrum shown in FIG. 10. As shown in FIG. 12, the amount of cumulative change in the spectrum increases approximately linearly with the amount of polishing. Therefore, the progress of polishing can be grasped according to the method of this embodiment. The amount of cumulative change in the spectrum shown in FIG. 12 was calculated using the equation (11) and the equation (13). The equation (15), the equation (16), or the equation (17) may be used, instead of the equation (11). In this case also, the same results can be obtained.

Figure 13:
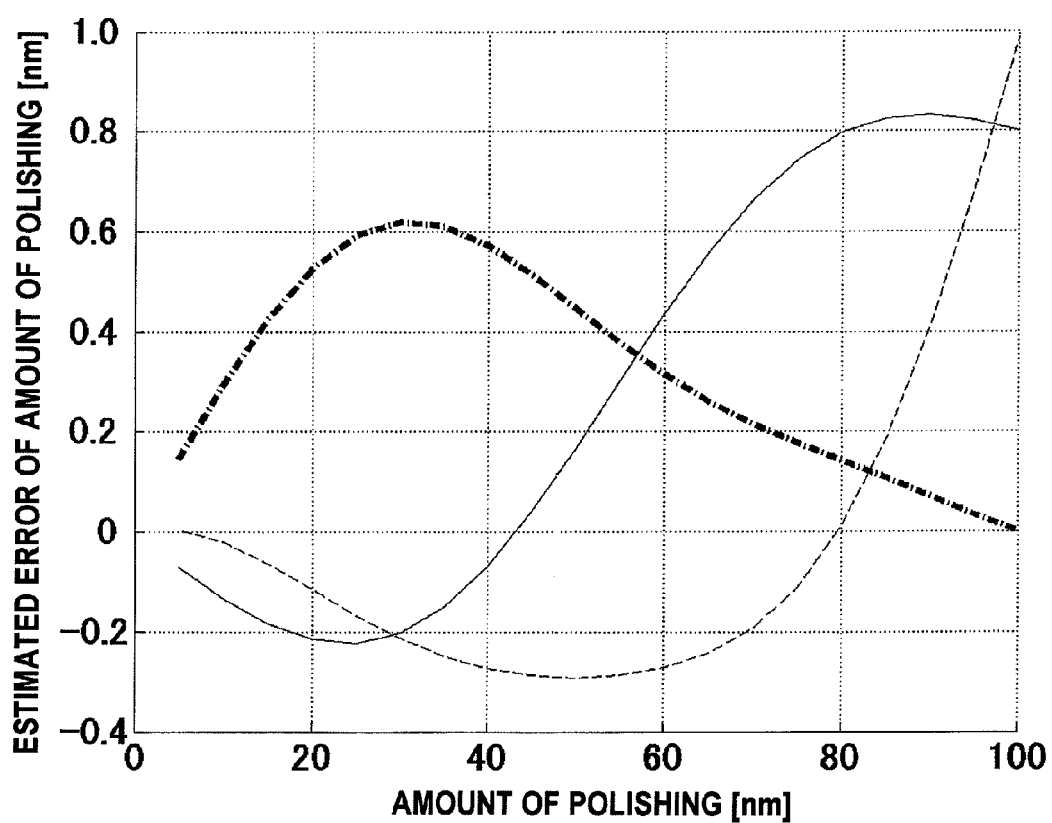
FIG. 13 is a graph showing estimated error of the amount of polishing obtained from polishing simulation of three substrates each having a structure shown in FIG. 9, the first substrate having a lower $SiO_2$ film with a thickness of 450 nm, the second substrate having a lower $SiO_2$ film with a thickness of 500 nm, the third substrate having a lower $SiO_2$ film with a thickness of 550 nm.

FIG. 13 is a graph showing estimated error of the amount of polishing obtained from polishing simulation of three substrates each having the structure shown in FIG. 9. The first substrate has a lower $SiO_2$ film (see FIG. 9) with a thickness of 450 nm, the second substrate has a lower $SiO_2$ film with a thickness of 500 nm, and the third substrate has a lower $SiO_2$ film with a thickness of 550 nm. The estimated error shown in FIG. 13 was calculated using the equation (11), the equation (13), and the equation (18). The equation (15), the equation (16), or the equation (17) may be used, instead of the equation (11).

The calculation of the error was on the basis of the substrate whose lower $SiO_2$ film has a thickness of 500 nm. The amount of cumulative change in the spectrum $A(\theta)$ obtained with respect to this substrate at the polishing end point corresponds to the amount of polishing 100 nm. Using the thickness of the lower $SiO_2$ film as a subscript, the error in each case is expressed in the same manner as that of FIG. 7A through FIG. 7D as follows.

$$E_{500}(\theta)=A_{500}(\theta)/A_{500}(100 \text{ nm})\times 100 \text{ nm} - (200 \text{ nm} - \theta) \quad (19)$$

$$E_{450}(\theta)=A_{450}(\theta)/A_{500}(100 \text{ nm})\times 100 \text{ nm} - (200 \text{ nm} - \theta) \quad (20)$$

$$E_{550}(\theta)=A_{550}(\theta)/A_{500}(100 \text{ nm})\times 100 \text{ nm} - (200 \text{ nm} - \theta) \quad (21)$$

A thick dashed line in FIG. 13 represents error of the amount of polishing in the case where the lower $SiO_2$ film has a thickness of 500 nm. A thin dotted line in FIG. 13 represents error of the amount of polishing in the case where the lower $SiO_2$ film has a thickness of 450 nm. A thin solid line in FIG. 13 represents error of the amount of polishing in the case where the lower $SiO_2$ film has a thickness of 550 nm. In any cases, the estimated error of the amount of polishing is within plus or minus 1 nm, which shows satisfactory accuracy in the practical use for estimating the amount of polishing. Therefore, by preparing in advance a relationship between the amount of cumulative change in the spectrum and the amount of polishing from actual polishing of one substrate (in this example, the substrate having the lower $SiO_2$ film with a thickness of 500 nm), it is possible to accurately determine the amount of polishing with respect to other substrates having different thickness of the lower $SiO_2$ film (in this example, the substrate having the lower $SiO_2$ film with a thickness of 450 nm, and the substrate having the lower $SiO_2$ film with a thickness of 550 nm) during polishing.

In the polishing process for adjusting the height of the Cu interconnects, the barrier layer is, in fact, formed on the uppermost dielectric film, as shown in FIG. 8, and typically the copper interconnects and the barrier layer are polished successively. Thus, in order to apply the method of the embodiment, it is preferable to detect a removal point of the barrier layer using an ammeter for current of the motor for rotating the polishing table, an eddy current sensor, or an optical sensor, and to start calculating the amount of cumulative change in the spectrum from the removal point of the barrier layer. As previously discussed, in the polishing process for adjusting the height of the Cu interconnects, the wavelength of the local extremum point does not vary greatly due to the influence of the etching stop layer. Therefore, the embodiment of the method utilizing the amount of change in the spectrum in its entirety is particularly advantageous.

Figure 14:
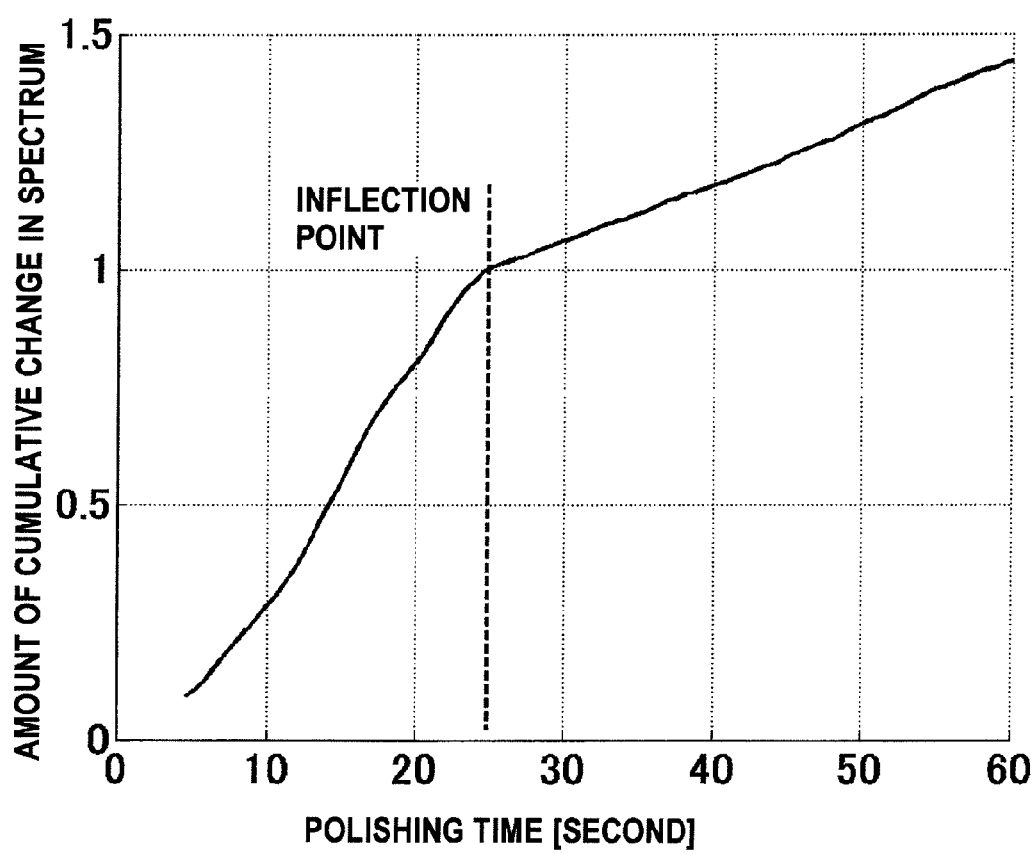
FIG. 14 is a diagram created by plotting temporal change in the amount of cumulative change in the spectrum obtained by actual polishing of the substrate having a structure shown in FIG. 8.
Figure 15:
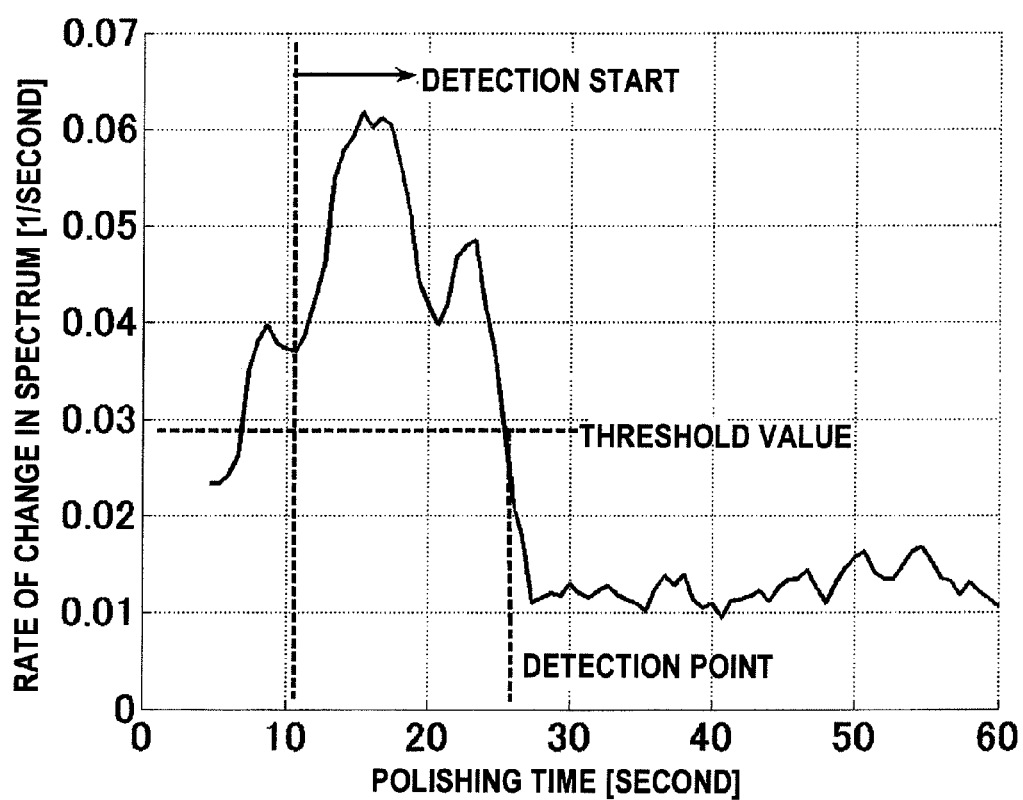
FIG. 15 is a diagram showing an example of a method of detecting an inflection point of the amount of cumulative change in the spectrum.

FIG. 14 is a diagram created by plotting temporal change in the amount of cumulative change in the spectrum obtained by actual polishing of the substrate having the structure shown in FIG. 8. The amount of cumulative change in the spectrum was calculated using the equation (3) and the equation (5). A slope (or gradient) of the amount of cumulative change in the spectrum changes after 20 seconds have elapsed from the polishing start, thus creating an inflection point. This inflection point corresponds to the removal point of the barrier layer described above. Therefore, by detecting the inflection point of the amount of cumulative change in the spectrum during polishing, the removal point of the barrier layer can be determined. FIG. 15 is a diagram showing an example of a method of detecting the inflection point of the amount of cumulative change in the spectrum. The graph shown in FIG. 15 is a graph created by plotting the temporal change in the amount of change in the spectrum per unit time calculated from the equation (3), i.e., the rate of change in the spectrum. The detection is started from a point of time obviously earlier than the barrier layer removal point, and a point of time when the amount of change in the spectrum decreases below a predetermined threshold value is determined to be the removal point of the barrier layer.

Instead of the equation (3), it is possible to use other equation, e.g., the equation (2), the equation (6), the equation (7), the equation (9), or the equation (10), for calculating the amount of change in the spectrum. In these cases also, the removal point of the barrier layer appears as the inflection point of the amount of cumulative change in the spectrum. Therefore, the inflection point of the amount of cumulative change in the spectrum, i.e., the removal point of the barrier layer, can be detected in accordance with the method shown in FIG. 15 as well.

Figure 16:
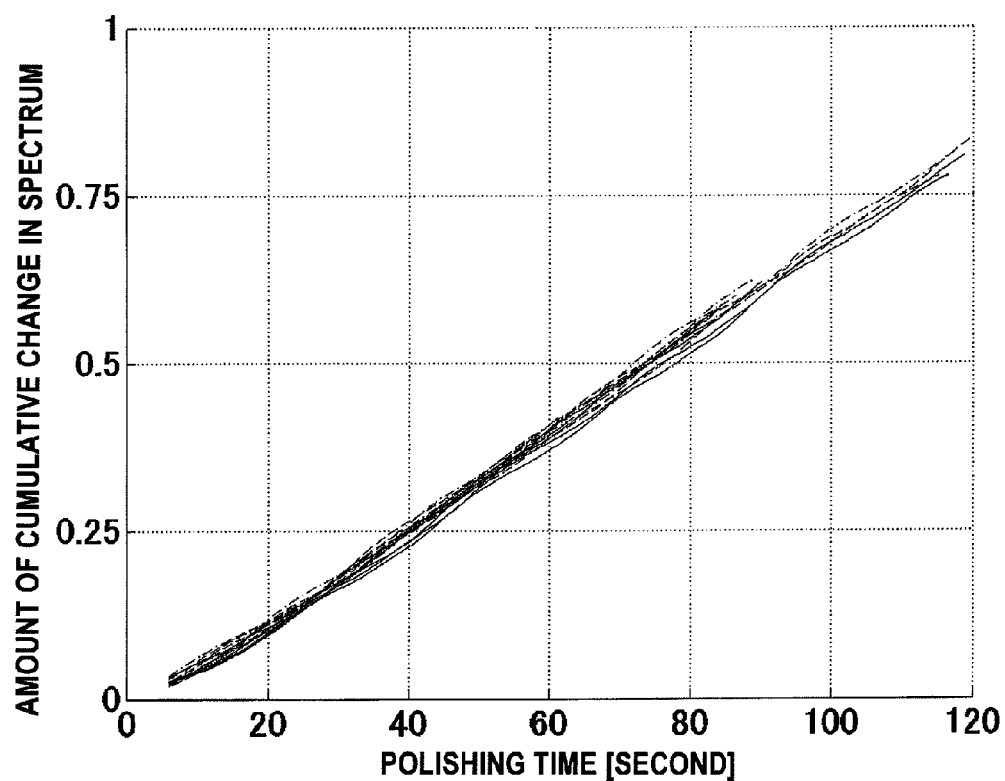
FIG. 16 is a graph showing the amount of cumulative change in the spectrum obtained by actually polishing 17 substrates having the same structure under the same polishing conditions except for polishing time.

Next, results of actually polishing plural substrates having the same structure will be described. FIG. 16 is a graph showing the amount of cumulative change in the spectrum obtained by actually polishing 17 substrates having the same structure. The 17 substrates were polished for different polishing times under the same polishing conditions. In polishing, a time taken for the polishing table to make one revolution was used as the time interval $\Delta t$. Specifically, the amount of change in the spectrum was calculated each time the polishing table made one revolution, and the amount of cumulative change in the spectrum was determined by integrating the amount of change in the spectrum obtained. In order to remove noise (or distortion) from the spectrum obtained, a moving average of spectra was calculated using latest plural spectral data, and the amount of change in the spectrum was calculated from the moving average of the spectra obtained. More specifically, each time the polishing table made one revolution, an average of the latest five spectra (which were obtained during five revolutions of the polishing table) was calculated and the amount of change in the spectrum was calculated from the average of the spectra obtained. In the graph shown in FIG. 16, a vertical axis represents the amount of cumulative change in the spectrum, and a horizontal axis represents polishing time (second). It can be seen from the graph of FIG. 16 that the amount of cumulative change in the spectrum increases approximately linearly with the polishing time. Therefore, by monitoring the amount of cumulative change in the spectrum during polishing, the progress of polishing can be grasped.

In the case of applying the moving average method as described above, the amount of change in the spectrum at each point of time is calculated through a certain calculation period, which is determined by the sum of a moving average time period and the time interval $\Delta t$ for calculating the amount of change in the spectrum. Therefore, it can be said that the amount of change in the spectrum obtained at each point of time is a value that represents the amounts of change in the spectrum in the calculation period just before that point of time.

Figure 17:
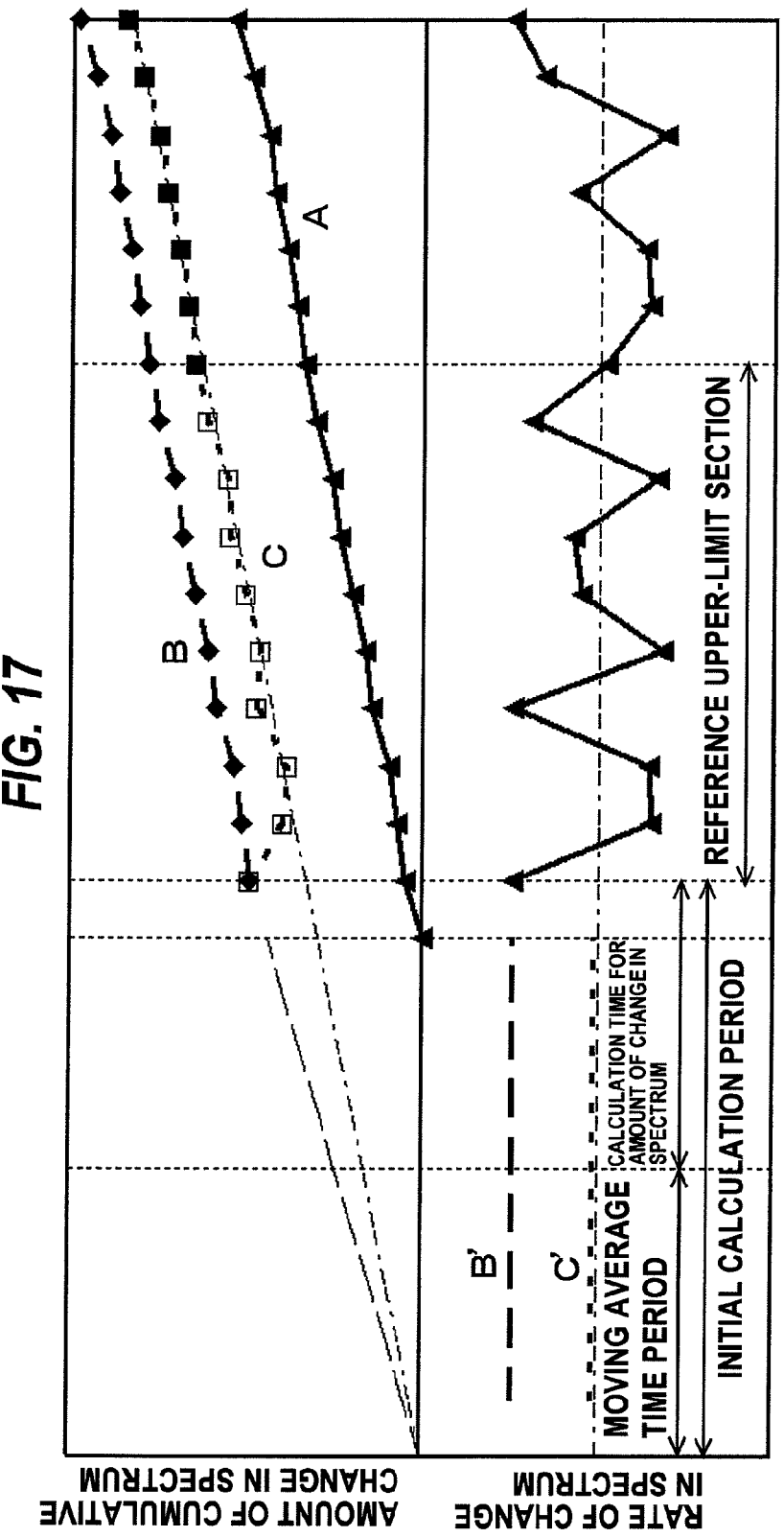
FIG. 17 is a diagram illustrating a method of establishing an initial value of the amount of cumulative change in the spectrum.

It is not possible to calculate the amount of change in the spectrum until the above-described calculation period has elapsed from the polishing start point. The existence of such calculation period poses a problem of how to establish an initial value of the amount of cumulative change in the spectrum at a point of time when the calculation period has elapsed from the polishing start point. An approach for establishing the initial value of the amount of cumulative change in the spectrum will be described with reference to FIG. 17. In FIG. 17, the amount of change in the spectrum per unit time (i.e., the rate of change in the spectrum) is plotted in a lower region of a diagram, and the amount of cumulative change in the spectrum is plotted in an upper region. Each of marks on the diagram represents a value calculated each time the polishing table makes one revolution.

In FIG. 17, the calculation period from the polishing start point is described as an initial calculation period. As described above, at each point of time after the initial calculation period has elapsed, a value representing the calculation period just before each point of time is plotted as the rate of change in the spectrum, and an accumulated value of the rate of change in the spectrum is plotted as the amount of cumulative change in the spectrum.

Symbol A in FIG. 17 indicates the amount of cumulative change in the spectrum obtained on the assumption that, from the polishing start point to a point of time just before the initial calculation period elapses, the rate of change in the spectrum is zero. Since the amount of cumulative change in the spectrum is given by integrating (i.e., adding up) the actual rate of change in the spectrum, the amount of cumulative change in the spectrum increases monotonically in a stable manner in many cases. The amount of cumulative change in the spectrum indicated by the symbol A is suitable for a case where the variation in the polishing rate between substrates is small, particularly in the initial stage of polishing. However, the amount of cumulative change in the spectrum indicated by the symbol A does not fully reflect the amount of polishing in the initial calculation period, and therefore shows offset values.

Symbol B in FIG. 17 indicates the amount of cumulative change in the spectrum obtained on the assumption that, from the polishing start point to a point of time just before the initial calculation period elapses, the rate of change in the spectrum is equal to a value B' at a point of time when the initial calculation period has elapsed. As described above, the value B' can be regarded as a value that represents the initial calculation period, and has a certain rationality. However, there is a problem that, compared with other values at points of time after the initial calculation period, the value B' is reflected greatly in the amount of cumulative change in the spectrum. For example, the rate of change in the spectrum could vary greatly by the influence of nonuniformity of the film thickness or interconnect density within the substrate surface, thus resulting in a large error of the value B' from an average level. In such a case, the error of the value B' is emphasized and as a result the amount of cumulative change in the spectrum obtained may show a value deviated from an actual amount of polishing.

Symbol C in FIG. 17 indicates the amount of cumulative change in the spectrum obtained on the assumption that, from the polishing start point to a point of time just before the initial calculation period elapses, the rate of change in the spectrum is equal to an average of the rate of change in the spectrum obtained after the lapse of the initial calculation period. The calculation of the average of the rate of change in the spectrum is started from a point of time when the initial calculation period has elapsed and is continued until a predetermined reference upper-limit section elapses. Specifically, at each point of time in the reference upper-limit section, the average of the rate of change in the spectrum, obtained up to that point of time, is calculated each time the rate of change in the spectrum is calculated. At each point of time after the reference upper-limit section has elapsed, an average of the rate of change in the spectrum calculated at the end point of the reference upper-limit section is used as the rate of change in the spectrum in the initial calculation period. In FIG. 17, the average of the rate of change in the spectrum calculated at the end point of the reference upper-limit section is shown as C'.

Further, the amount of cumulative change in the spectrum is also recalculated at each point of time in the reference upper-limit section. In other words, the amount of cumulative change in the spectrum is recalculated each time the rate of change in the spectrum is calculated such that the amount of cumulative change in the spectrum is zero at the polishing start point when data of the amount of cumulative change in the spectrum in the initial calculation period are determined by extrapolation based on the average of the rate of change in the spectrum. With the above-described operations, even if the rate of change in the spectrum fluctuates greatly, a maximum likelihood value can be obtained at each point of time. There may be some cases, however, where the amount of cumulative change in the spectrum obtained fluctuates up and down for a while after the lapse of the initial calculation period. There may also be cases where the polishing rate varies greatly during polishing, particularly in an early stage of polishing. In these cases, the method shown by the symbol C is not suitable. Although the example shown in FIG. 16 is based on the method according to the symbol C, the fluctuation of the amount of cumulative change in the spectrum at the initial stage of polishing does not appear on the graph, because the fluctuation of the rate of change in the spectrum is small. In the substrate polishing process starting from the barrier layer as shown in FIG. 8, the polishing start point in the above explanation can be replaced with a detection point of removal of the barrier layer.

Figure 18:
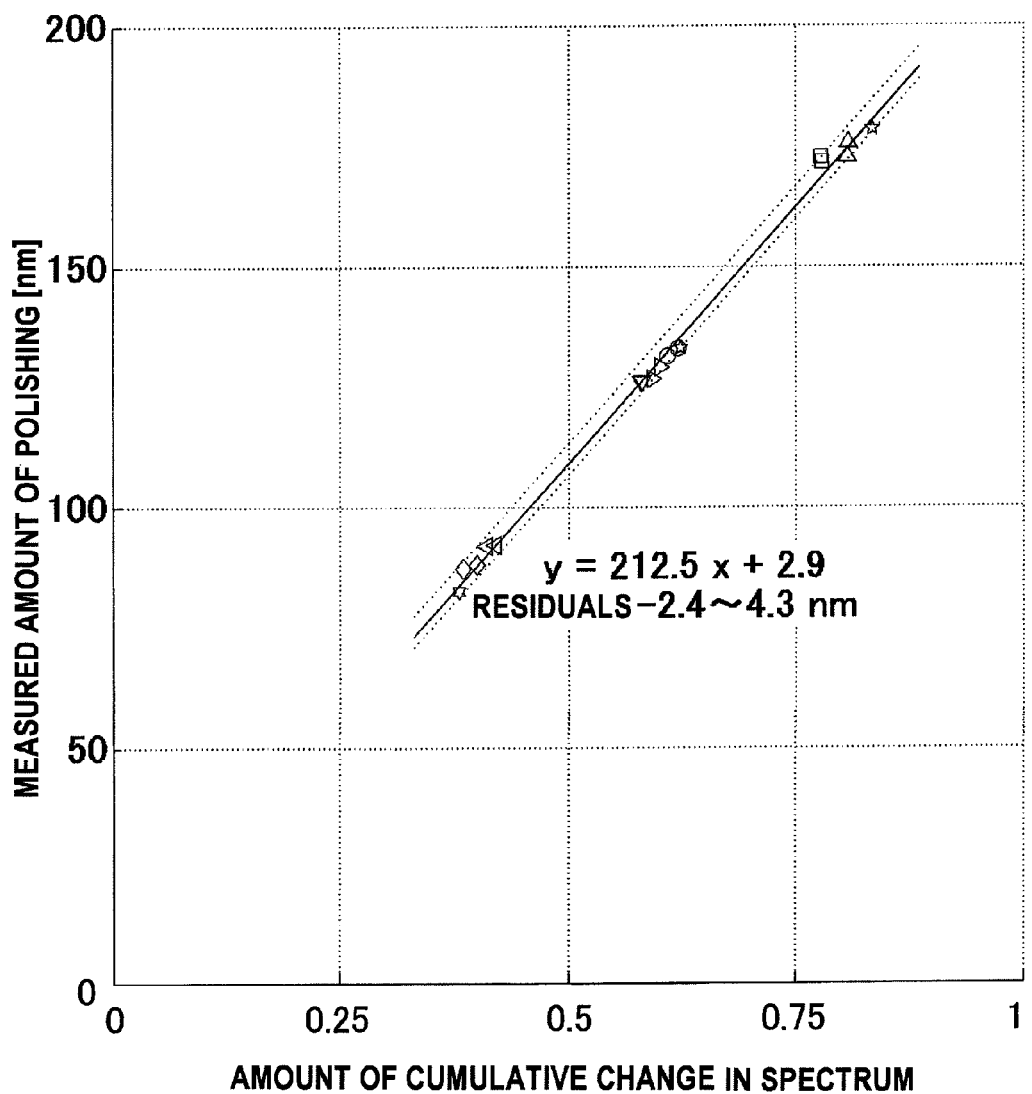
FIG. 18 is a graph showing a relationship between the amount of cumulative change in the spectrum at the polishing end point with respect to each of the 17 substrates and measured amount of polishing with respect to each substrate obtained from film-thickness measurement conducted before and after polishing.

FIG. 18 is a graph showing a relationship between the amount of cumulative change in the spectrum at the polishing end point with respect to each of the 17 substrates and measured amount of polishing with respect to each substrate obtained from film-thickness measurement conducted before and after polishing. Typically, last measurement data obtained during polishing is used for the amount of cumulative change in the spectrum at the polishing end point. However, due to some causes including checking of the polishing end point detection and data communication, a delay time may exist between when the polishing monitoring device detects the polishing end point and when the last measurement data is obtained. In such a case, previous measurement data, which is obtained earlier than the last measurement data by the delay time, may be used. Alternatively, the amount of cumulative change in the spectrum corresponding to the delay time may be estimated from the amount of change in the spectrum in the polishing final stage, and the estimated value may be added to the amount of cumulative change in the spectrum calculated based on measurement data obtained earlier than the polishing end point by the delay time. This approach can also be applied to a case where the delay time is supposed to exist between when polishing is started and when the first measurement data is obtained. Specifically, the amount of cumulative change in the spectrum corresponding to the delay time is estimated from the amount of change in the spectrum in the polishing initial stage, and the estimated value is added to the amount of cumulative change in the spectrum calculated based on measurement data. The graph in FIG. 18 expresses a regression line extending near measured points with respect to the 17 substrates. This regression line can be determined by least squares method. Letting x be the amount of cumulative change in the spectrum and letting y be the measured amount of polishing (actual amount of polishing), the regression line is expressed as $y=212.5x+2.9$. Residuals, each of which indicates a deviation of each measured point from the regression line, are within the range of −2.4 nm to 4.3 nm. A y-intercept of the regression line is 2.9 nm. Therefore, the regression line extends near the origin. In the case where the amount of cumulative change in the spectrum corresponding to the delay time is estimated to determine the relationship between the amount of cumulative change in the spectrum and the amount of polishing or to determine the relational expression as discussed above, the estimated value is added to the amount of cumulative change in the spectrum to provide monitoring data during monitoring of the actual polishing as well.

When polishing a new substrate of the same type, the amount of polishing at each point of time can be determined during polishing by substituting the amount of cumulative change in the spectrum, obtained during polishing, into the above-described equation of the regression line. Therefore, the polishing end point can be determined from the comparison between a present amount of polishing and a target amount of polishing. Further, in the case where a specification of initial film thickness of substrates is known and error of the initial film thickness is small between the substrates or where the initial film thickness can be measured prior to polishing of each substrate, a remaining film thickness can be determined by subtracting the amount of polishing from the initial film thickness. Further, it is also possible to determine the polishing end point from the comparison between the remaining film thickness and the target film thickness.

In the above-described example, the regression line is obtained by applying the least squares method based on the 17 measured points. The origin of the coordinate axes (i.e., the amount of cumulative change in the spectrum is zero, the measured amount of polishing is zero) may be added to the 17 measured points when applying the least squares method. The regression line may be determined on the assumption that the regression line extends through the origin. To create the regression line using only the measured points like the above example, at least two measured points are needed. This means that at least two substrates should be polished in advance. In contrast, the approach in which the origin of the coordinate axes is added to the measured points when applying the least squares method only requires at least one substrate to be polished in advance. In the case of polishing only one substrate, a regression line that extends through the origin of the coordinate axes and one measured point is created. It is preferable that the regression line extend near the origin of the coordinate axes. However, even if the regression line deviates from the origin to some degree due to some causes, such as difference in location between a measurement point for film thickness and a measurement point for monitoring during polishing, the polishing end point can be detected with an adequate accuracy, so long as the regression line (i.e., regression equation) has small residuals in a region around the target amount of polishing.

The embodiments discussed above are examples in which the amount of cumulative change in the spectrum is approximately proportional to the amount of polishing. However, there is a case where the amount of cumulative change in the spectrum is not proportional to the amount of polishing. For example, in the polishing process as shown in FIG. 8 for adjusting the Cu interconnect resistance (i.e., the height of the Cu interconnects), the spectrum per unit amount of polishing varies greatly after the interconnect height is reduced to about less than 65 nm. In particular, the spectrum in the wavelength range of not less than 600 nm varies greatly. Even in such a case, by limiting the wavelength range appropriately, e.g., from 400 nm to 500 nm, it is possible to obtain the amount of cumulative change in the spectrum corresponding to the amount of polishing. It is also possible to perform regression analysis by determining a nonlinear equation, such as quadratic polynomial, indicating the relationship between the amount of cumulative change in the spectrum and the amount of polishing.

Figure 19:
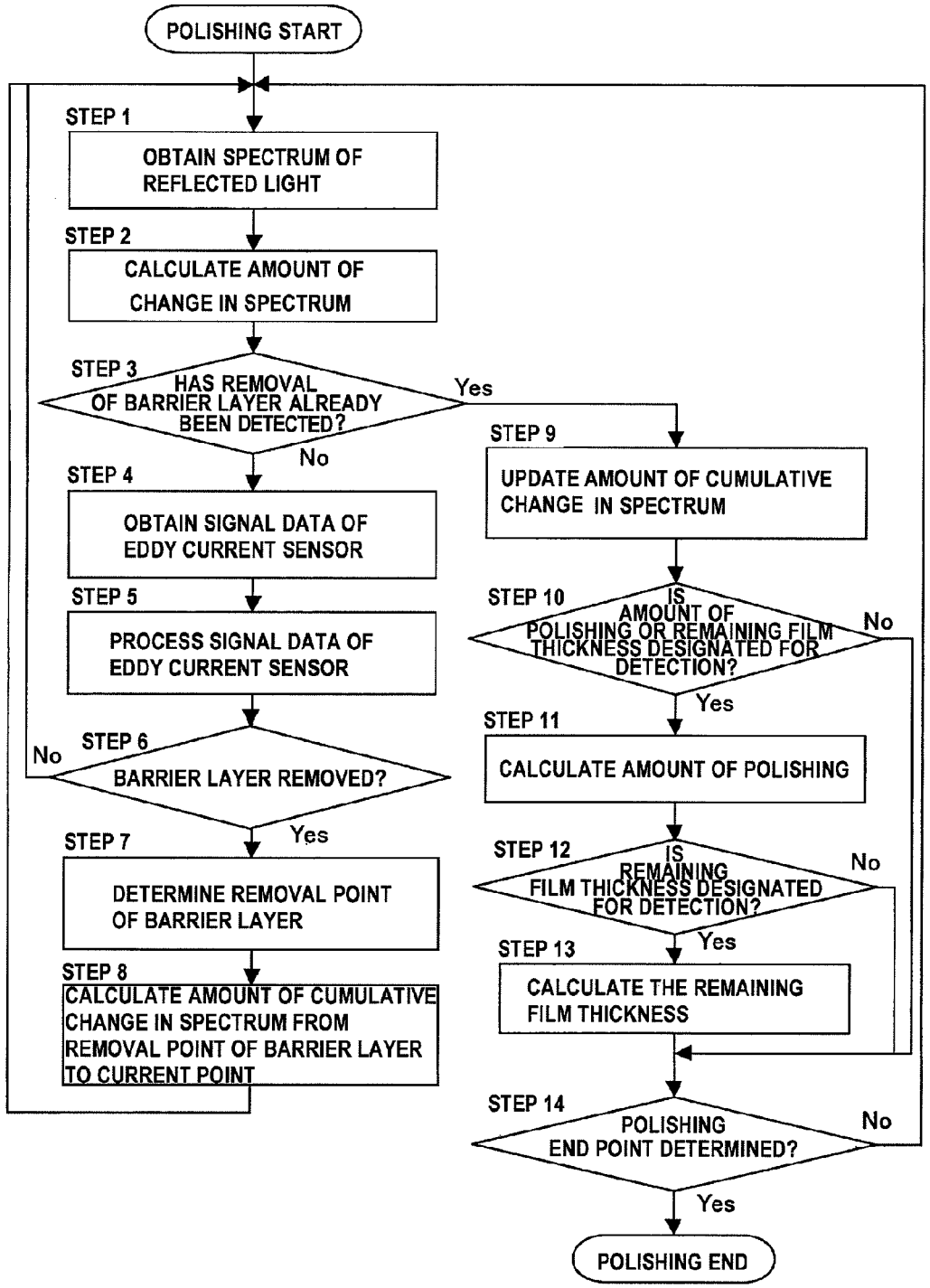
FIG. 19 is a flow chart showing a process flow diagram in a case where the embodiment of the method is applied to a polishing process for adjusting a height of copper interconnects.

FIG. 19 is a flow chart showing a process flow diagram in a case where the method according to the above-described embodiment is applied to the polishing process for adjusting the height of the copper interconnects. This flow chart shows sequential processes that includes: detecting removal of the barrier layer by the eddy current sensor; starting calculation of the amount of cumulative change in the spectrum from a removal point of the barrier layer (i.e., a point of time when the barrier layer is removed); and determining the polishing end point. These steps will be described below with reference to FIG. 19.

The spectrum of the reflected light from the substrate is obtained during polishing of the substrate (step 1), and the amount of change in the spectrum with respect to the predetermined time is calculated (step 2). In this example, the predetermined time is set to a time taken for the polishing table to make one revolution. Therefore, the step 1 and the step 2 are performed each time the polishing table makes one revolution.

The calculation of the amount of change in the spectrum is started before the barrier layer is removed. This is because of the following reasons. In the removal detection of the barrier layer using the eddy current sensor, various kinds of processes are performed for smoothing output signals of the eddy current sensor and checking the detection of a signal-changing point, thus causing a slight delay in detection of the removal of the barrier layer. Thus, as will be described later, when removal of the barrier layer is detected, the processing device 15 determines an actual point of time when the barrier layer is removed, and calculates the amount of cumulative change in the spectrum beginning retroactively from the actual point of time when the barrier layer is removed. The way of determining the point of time when the barrier layer is actually removed can be applied to the above-described example of detecting the removal of the barrier layer based on the rate of change in the spectrum as well.

The processing device 15 (see FIG. 2A) detects the removal of the barrier layer based on the output signal of the eddy current sensor. The processing device 15 checks whether the removal of the bather layer has already been detected or not (step 3). If the removal of the bather layer is not detected in a previous point of time, the processing device 15 obtains new output signal of the eddy current sensor (step 4) and performs a predetermined process (e.g., smoothing) on the newly obtained output signal (step 5). Further, the processing device 15 determines whether the barrier layer is removed or not based on the output signal processed (step 6).

If the removal of the barrier layer is detected, the processing device 15 determines a point of time when the barrier layer is removed (step 7). This point of time when the bather layer is removed (i.e., the removal point of the barrier layer) is determined by subtracting a predetermined time from a point of time when the removal of the barrier layer is determined in the step 6. This predetermined time is determined based on the delay time due to the smoothing process of the sensor signals and the checking process of the signal changing point as described above. The processing device 15 calculates the amount of cumulative change in the spectrum beginning from the determined removal point of the barrier layer to a current point of time. Then, the process goes back to the step 1.

If the removal of the bather layer has already been detected in the step 3, the amount of change in the spectrum at the current point of time is added to the existing amount of cumulative change in the spectrum, so that the amount of cumulative change in the spectrum is renewed (step 9). Monitoring of the polishing progress and determining of the polishing end point are performed using any one of the amount of cumulative change in the spectrum, the amount of polishing, and the film thickness. If the processing device 15 is designated to use the amount of polishing or the film thickness for determining the polishing end point (step 10), the processing device 15 calculates the amount of polishing based on the regression equation as described above (step 11). If the processing device 15 is designated to use the film thickness for determining the polishing end point (step 12), the processing device 15 calculates the remaining film thickness by subtracting the amount of polishing from the initial film thickness obtained in advance (step 13).

In accordance with the designation, the processing device 15 determines the polishing end point based on the amount of cumulative change in the spectrum, the amount of polishing, or the film thickness (step 14). Basically, the amount of cumulative change in the spectrum and the amount of polishing increase monotonically during polishing, and on the other hand the film thickness decreases monotonically during polishing. Therefore, a point of time when the amount of cumulative change in the spectrum, the amount of polishing, or the film thickness has reached a predetermined target value can be determined to be the polishing end point.

In this method, the progress of polishing is monitored based on the amount of change in the spectrum in its entirety. Therefore, this method can be applied to polishing of substrates having various structures. In particular, even in the case where the wavelengths of the local extremum points of the spectrum do not change greatly because of a small amount of polishing and because of multilayer transparent films having greatly different refractive indexes (e.g., like a polishing process for adjusting the height of copper interconnects), this method can accurately obtain the change in thickness of a film to be polished. Moreover, even if the substrate has a complicated multilayer structure, the amount of cumulative change in the spectrum, which is obtained by adding up the amount of change in the spectrum, increases monotonically during polishing, basically. Therefore, it is easy to grasp the progress of substrate polishing from the amount of cumulative change in the spectrum. Further, by simply comparing the amount of cumulative change in the spectrum with a predetermined target value or threshold value, the polishing end point can be detected easily.

If the spectrum measuring points within the surface of the substrate vary with time and if there are slight differences in the film thickness within the surface of the substrate, the film thickness may not necessarily decrease monotonically during polishing. It is possible to calculate an average of the spectral data obtained while the polishing table makes one revolution. However, if the film thickness is not uniform in a circumferential direction of the substrate, the film thickness may not decrease monotonically with respect to the time axis. Even in this case, by extending the above-described predetermined time for calculating the amount of change in the spectrum, the film thickness before and after the predetermined time can be regarded as decreasing monotonically. Alternatively, by calculating the moving average of the spectra, the corresponding film thickness can be regarded as decreasing monotonically.

In consideration of nonuniformity of the film thickness within the substrate surface, a trend of the amount of change in the spectrum during polishing, i.e., a plus or minus sign of the amount of change in the spectrum, may be discriminated. In the case where transparent films of a substrate have approximately the same optical constant, the behavior of the reflected light can be analyzed based on the theory of interference of light with respect to a single-layer film. Specifically, the wavelengths of the local extremum points (i.e., the local maximum points and the local minimum points) of the spectrum decrease with the decrease in the film thickness. Therefore, by tracking the wavelength of each local extremum point of the spectrum, it is possible to determine the sign (plus or minus) of the amount of change in the spectrum.

Figure 20:
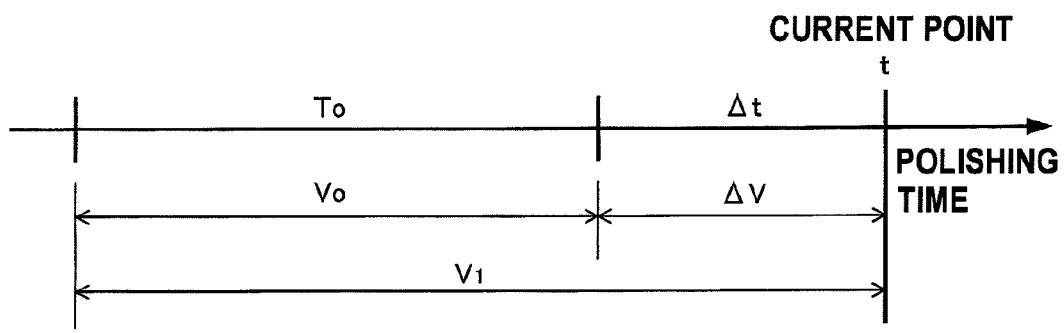
FIG. 20 is a diagram illustrating a process of determining plus or minus sign of an amount of change in the spectrum.
Figure 20:
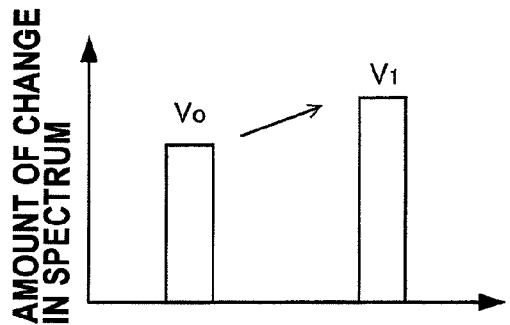
Figure 20:
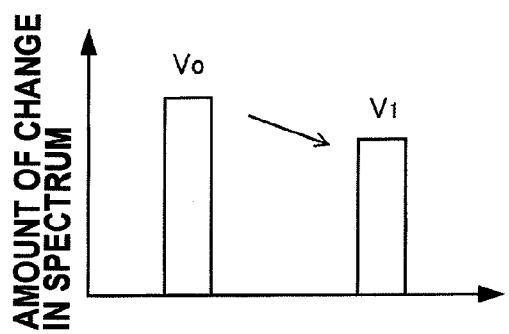

In contrast, like the substrates as shown in FIG. 8 and FIG. 9, when transparent films having greatly different optical constants exist, the wavelengths of the local extremum points of the spectrum do not change monotonically with the decrease in the film thickness. In such a case, it is possible to determine the plus or minus sign of the amount of change in the spectrum as follows. FIG. 20 is a diagram illustrating a process of determining plus or minus sign of the amount of change in the spectrum. In FIG. 20, $\Delta t$ represents interval for calculating the amount of change in the spectrum with respect to a current point of time t, and $T_O$ represents a predetermined sign reference interval preceding the interval $\Delta t$.

The amount of change in the spectrum (positive value) given by, for example, the equation (2) is calculated for each of the interval $\Delta t$, the interval $T_O$, and a total interval consisting of combination of the intervals $\Delta t$ and $T_O$. If an amount of change in the spectrum $V_1$ in the total interval is larger than an amount of change in the spectrum $V_O$ in the interval $T_O$ (i.e., $V_1 > V_O$), an amount of change in the spectrum $\Delta V$ in the interval $\Delta t$ is determined to have a plus sign (i.e., $\Delta V > 0$). Therefore, the film thickness is in a decreasing trend. In this case, the rate of change in the spectrum $\Delta V/\Delta t$ also has a plus sign. On the other hand, if the amount of change in the spectrum $V_1$ in the total interval is smaller than the amount of change in the spectrum $V_O$ in the interval $T_O$ (i.e., $V_1 < V_O$), the amount of change in the spectrum $\Delta V$ in the interval $\Delta t$ is determined to have a minus sign (i.e., $\Delta V < 0$). Therefore, the film thickness is in an increasing trend. In this case, the rate of change in the spectrum $\Delta V/\Delta t$ also has a minus sign.

Figure 21:
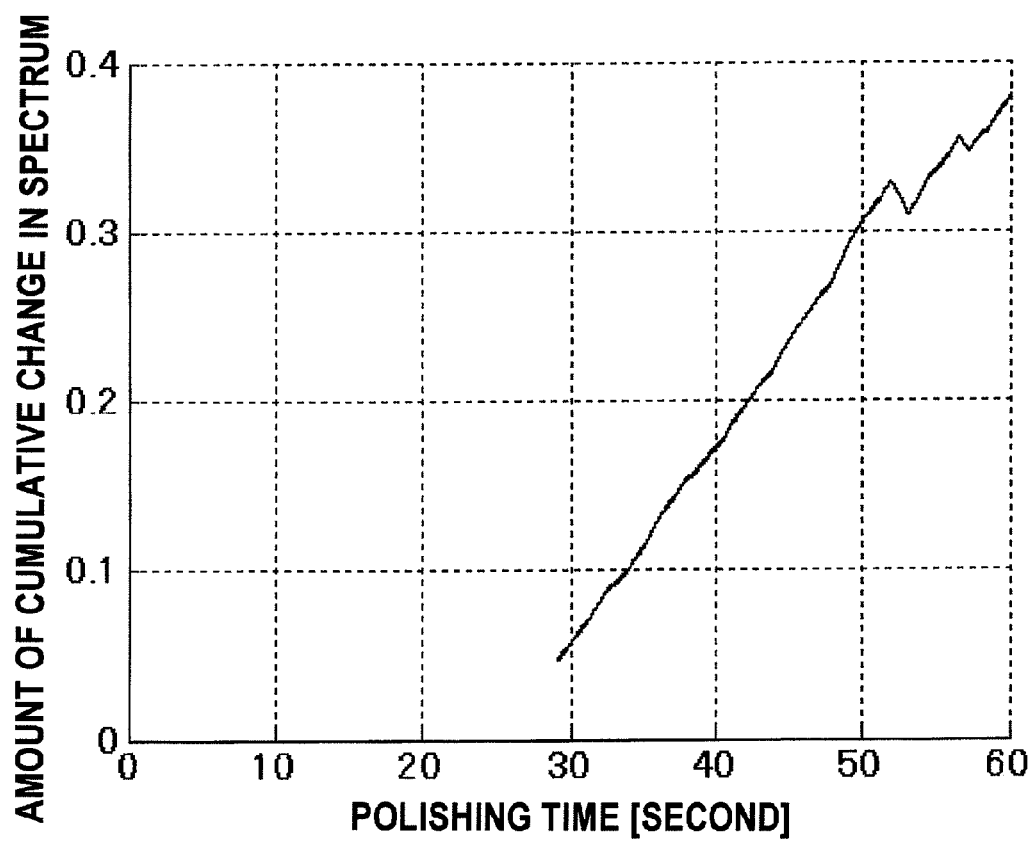
FIG. 21 is a diagram showing the amount of cumulative change in the spectrum obtained after a barrier layer of the substrate shown in FIG. 8 is removed.

There may be a case where the sign reference interval $T_O$ cannot be defined in the polishing initial stage. In such a case, an interval having the same length as the interval $T_O$ may be provided after the interval $\Delta t$. The sign of the amount of change in the spectrum is determined in the same process as described above, and "plus" sign, which has been provisionally assigned, is renewed. FIG. 21 is a diagram showing the amount of cumulative change in the spectrum obtained after the barrier layer of the substrate shown in FIG. 8 is removed. As can be seen from FIG. 21, the sign of the amount of change in the spectrum is changed to minus twice.

Figure 22A:
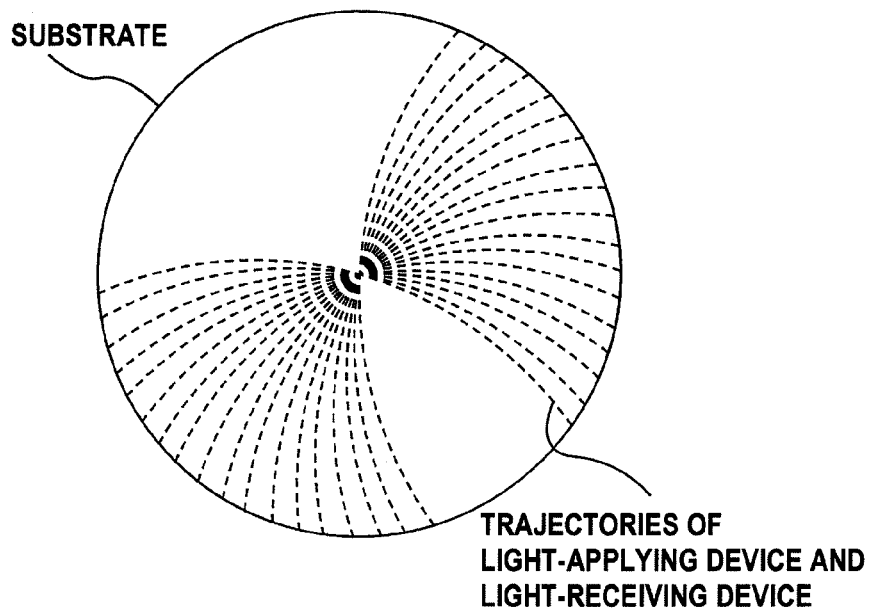
FIG. 22A is a view showing trajectories of a light-applying unit and a light-receiving unit described on a surface of the substrate when the polishing table and the top ring are rotated at 60 $min^{-1}$ and 61 $min^{-1}$, respectively.
Figure 22B:
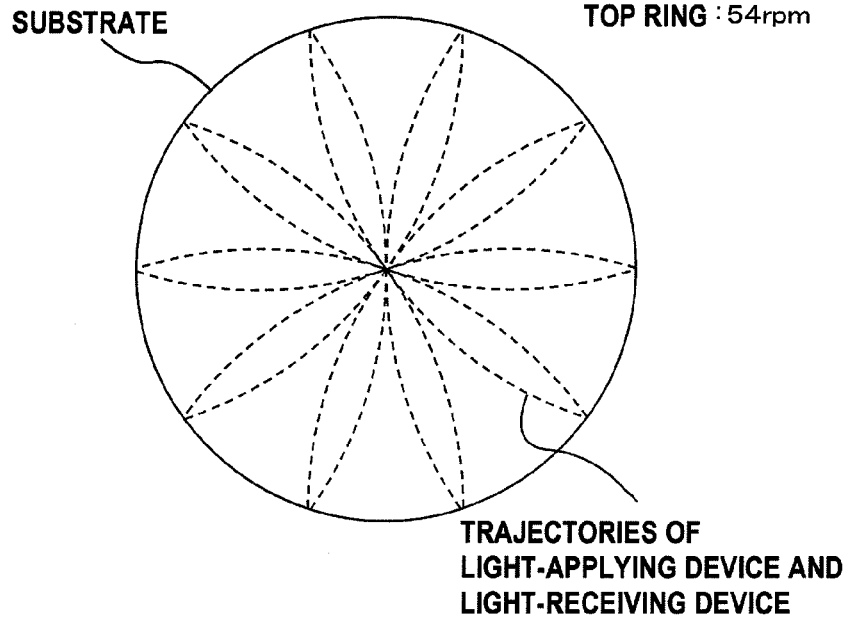
FIG. 22B is a view showing trajectories of the light-applying unit and the light-receiving unit described on the surface of the substrate when the polishing table and the top ring are rotated at 60 $min^{-1}$ and 54 $min^{-1}$, respectively.

In the case where the nonuniformity of the film thickness in the circumferential direction of the substrate could greatly affect the detection accuracy, it is preferable to adjust the rotational speed of the polishing table and the rotational speed of the top ring that holds the substrate. By adjusting these speeds, the influence of the nonuniform film thickness can be reduced. FIG. 22A is a view showing trajectories of the light-applying unit 11 and the light-receiving unit 12 (see FIG. 2A and FIG. 2B) described on the surface of the substrate when the polishing table and the top ring of the polishing apparatus shown in FIG. 2B are rotated at 60 min$^{-1}$ and 61 min$^{-1}$, respectively. FIG. 22B is a view showing trajectories of the light-applying unit 11 and the light-receiving unit 12 described on the surface of the substrate when the polishing table and the top ring are rotated at 60 min$^{-1}$ and 54 min$^{-1}$, respectively.

In the case of FIG. 22A, the trajectories of the light-applying unit 11 and the light-receiving unit 12 move little by little with the rotation of the polishing table. In contrast, in the case of FIG. 22B, the top ring makes nine revolutions while the polishing table makes ten revolutions, and the light-applying unit 11 and the light-receiving unit 12 are retuned to their original positions within the substrate surface. This means that the spectrum obtained before the polishing table makes ten revolutions and the spectrum obtained at the current point of time are obtained at the same position on the surface of the substrate. Therefore, in the example of FIG. 22B, it is preferable to determine the amount of change in the spectrum at each point of time during polishing from the comparison between the spectrum obtained before the polishing table makes ten revolutions and the spectrum obtained at the current point of time. By comparing the spectra obtained at the same position on the substrate, accurate amount of polishing can be determined. Alternatively, it is also possible to calculate at each point of time an average of latest spectra obtained while the polishing table makes ten revolutions and to calculate the amount of change in the spectrum from the average spectrum obtained. Because the light-applying unit 11 and the light-receiving unit 12 scan the substrate surface in its entirety while the polishing table makes ten revolutions, accurate results can be obtained.

Figure 23:
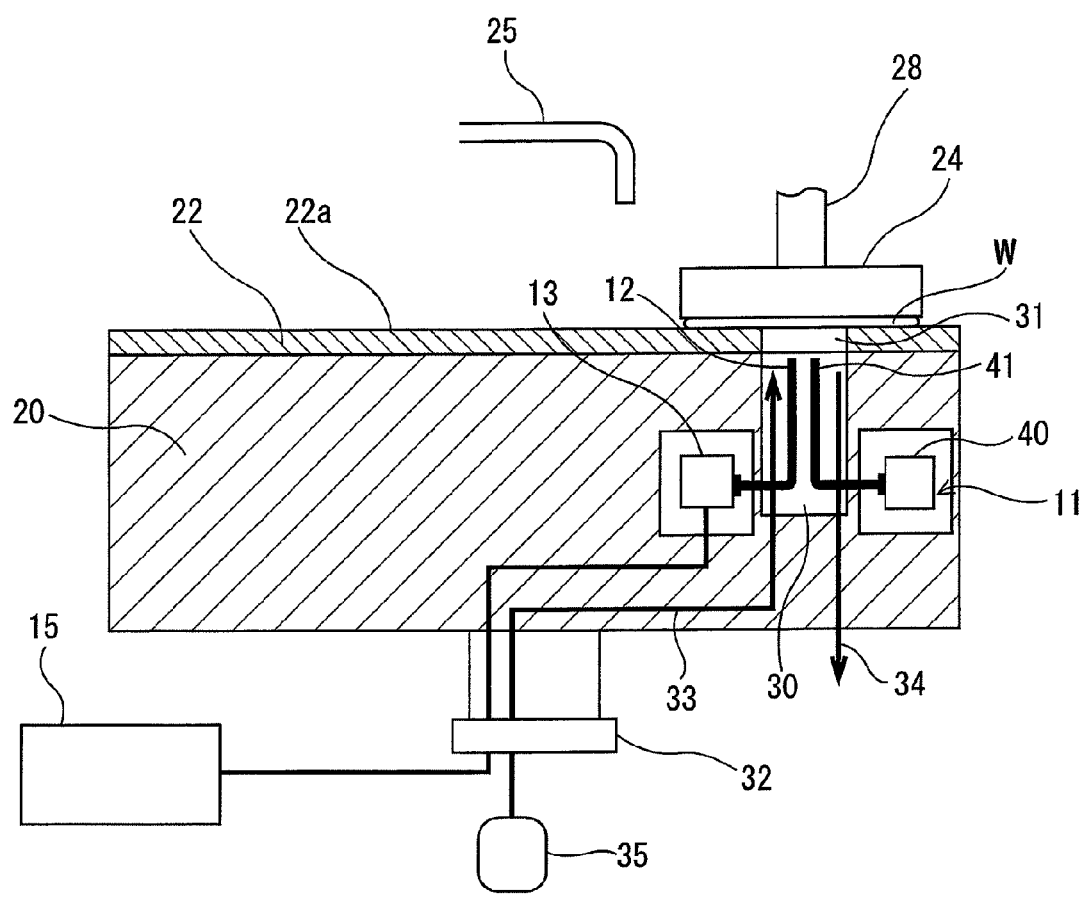
FIG. 23 is a cross-sectional view schematically showing a polishing apparatus having a polishing monitoring device capable of performing the polishing monitoring method and the polishing end point detection method according the embodiment of the present invention.

FIG. 23 is a cross-sectional view schematically showing a polishing apparatus having the polishing monitoring device capable of performing the polishing monitoring method and the polishing end point detection method according the embodiment of the present invention as described above. As shown in FIG. 23, the polishing apparatus includes the polishing table 20 for supporting the polishing pad 22 thereon, a top ring 24 configured to hold a substrate W and to press the substrate W against the polishing pad 22, and a polishing liquid supply mechanism 25 configured to supply a polishing liquid (slurry) onto the polishing pad 22. The polishing table 20 is coupled to a motor (not shown in the drawing) provided below the polishing table 20, so that the polishing table 20 can be rotated about its own axis. The polishing pad 22 is secured to an upper surface of the polishing table 20.

The polishing pad 22 has an upper surface 22a, which provides a polishing surface for polishing the substrate W. The top ring 24 is coupled to a motor and an elevating cylinder (not shown in the drawing) via a top ring shaft 28. This configuration allows the top ring 24 to move vertically and to rotate about the top ring shaft 28. The top ring 24 has a lower surface which is configured to hold the substrate W by a vacuum suction or the like.

The substrate W, held on the lower surface of the top ring 24, is rotated by the top ring 24, and is pressed by the top ring 24 against the polishing pad 22 on the rotating polishing table 20. During the sliding contact between the substrate W and the polishing pad 22, the polishing liquid is supplied onto the polishing surface 22a of the polishing pad 22 from the polishing liquid supply mechanism 25. The surface of the substrate W is polished in the presence of the polishing liquid between the surface of the substrate W and the polishing pad 22. A relative movement mechanism for providing the sliding contact between the substrate W and the polishing pad 22 is constructed by the polishing table 20 and the top ring 24.

The polishing table 20 has a hole 30 whose upper end lying in the upper surface of the polishing table 20. The polishing pad 22 has a through-hole 31 at a position corresponding to the hole 30. The hole 30 and the through-hole 31 are in fluid communication with each other. An upper end of the through-hole 31 lies in the polishing surface 22a. The hole 30 is coupled to a liquid supply source 35 via a liquid supply passage 33 and a rotary joint 32. During polishing, the liquid supply source 35 supplies water (preferably pure water) as a transparent liquid into the hole 30. The water fills a space formed by the lower surface of the substrate W and the through-hole 31, and is expelled therefrom through a liquid discharge passage 34. The polishing liquid is discharged with the water and thus a path of the light is secured. The liquid supply passage 33 is provided with a valve (not shown in the drawing) configured to operate in conjunction with the rotation of the polishing table 20. The valve operates so as to stop the flow of the water or reduce the flow of the water when the substrate W is not located above the through-hole 31.

The polishing apparatus has the polishing monitoring device for monitoring the progress of polishing and detecting the polishing endpoint according to the above-described method. This polishing monitoring device also serves as a polishing end point detection device. The polishing monitoring device includes the light-applying unit 11 configured to direct the light to the surface, to be polished, of the substrate W, optical fiber 12 as the light-receiving unit configured to receive the reflected light from the substrate W, the spectroscope 13 configured to decompose the reflected light, received by the optical fiber 12, according to the wavelength and to measure the intensity of the reflected light over a predetermined wavelength range, and the processing device 15 configured to produce the spectrum from the measurement data obtained by the spectroscope 13 and to monitor the progress of polishing of the substrate based on the change in the spectrum. The spectrum indicates the intensity of the light distributed over the predetermined wavelength range and is expressed as a line graph indicating a relationship between intensity of the light and wavelength.

The light-applying unit 11 includes a light source 40 and an optical fiber 41 coupled to the light source 40. The optical fiber 41 is a light-transmitting element for directing the light of the light source 40 to the surface of the substrate W. The optical fiber 41 extends in the hole 30 from the light source 40 to reach a position near the surface of the substrate W to be polished. The optical fiber 41 and the optical fiber 12 have tip ends, respectively, facing the center of the substrate W held by the top ring 24, so that the light is applied to regions including the center of the substrate W each time the polishing table 20 rotates, as shown in FIG. 2B.

The light source 40 is configured to emit multi-wavelength light. A light emitting diode (LED), a halogen lamp, a xenon lamp, or the like can be used for the light source 40. The optical fiber 41 and the optical fiber 12 are arranged in parallel with each other. The tip ends of the optical fiber 41 and the optical fiber 12 are arranged so as to face in a direction perpendicular to the surface of the substrate W, so that the optical fiber 41 directs the light to the surface of the substrate W in the perpendicular direction.

During polishing of the substrate W, the light-applying unit 11 applies the light to the substrate W, and the optical fiber 12 receives the reflected light from the substrate W. During the application of the light, the hole 30 is supplied with the water, whereby the space between the tip ends of the optical fibers 41 and 12 and the surface of the substrate W is filled with the water. The spectroscope 13 measures the intensity of the reflected light at each wavelength, and the processing device 15 produces the spectrum that indicates the relationship between intensity of the light and wavelength. Further, the processing device 15 calculates the amount of cumulative change in the spectrum from the spectrum of the reflected light, monitors the progress of the polishing based on the amount of cumulative change in the spectrum, and determines the polishing end point, as discussed above.

Figure 24:
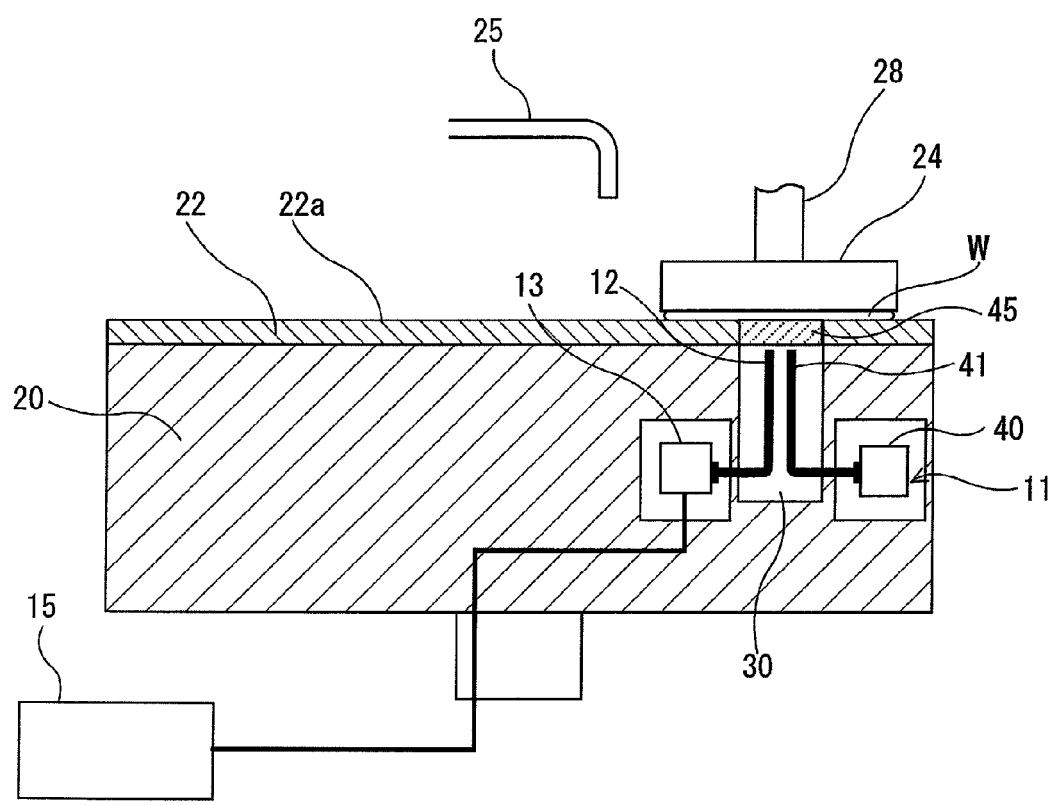
FIG. 24 is a cross-sectional view showing a modified example of the polishing apparatus shown in FIG. 23.

FIG. 24 is a cross-sectional view showing a modified example of the polishing apparatus shown in FIG. 23. In the example shown in FIG. 24, the liquid supply passage, the liquid discharge passage, and the liquid supply source are not provided. Instead, a transparent window 45 is provided in the polishing pad 22. The optical fiber 41 of the light-applying unit 11 directs the light through the transparent window 45 to the surface of the substrate W on the polishing pad 22, and the optical fiber 12 as the light-receiving unit receives the reflected light from the substrate W through the transparent window 45. The other structures are the same as those of the polishing apparatus shown in FIG. 23.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

What is claimed is:

1. A method of monitoring progress of polishing of a substrate having a film, said method comprising:
   directing light to the substrate during polishing of the substrate;
   receiving reflected light from the substrate;
   measuring an intensity of the reflected light at each of a plurality of wavelengths;
   producing a spectrum indicating a relationship between intensity and wavelength from measured values of the intensity;
   calculating an amount of change in the spectrum per predetermined time;
   integrating the amount of change in the spectrum with respect to polishing time to obtain an amount of cumulative change in the spectrum; and
   monitoring the progress of polishing of the substrate based on the amount of cumulative change in the spectrum.

2. The method according to claim 1, wherein the amount of change in the spectrum is a magnitude of relative change between two spectra produced at two different points of time.

3. The method according to claim 2, wherein the magnitude of relative change is a root mean square of a difference in intensity between the two spectra in a predetermined wavelength range.

4. The method according to claim 2, wherein the magnitude of relative change is an average of absolute values of a difference in intensity between the two spectra in a predetermined wavelength range.

5. The method according to claim 2, wherein the amount of change in the spectrum is a rate of change in the spectrum obtained by dividing the magnitude of relative change by a time interval between the two different points of time.

6. The method according to claim 1, wherein the amount of change in the spectrum has a plus or minus sign.

7. The method according to claim 1, wherein the spectrum is a spectrum indicating relationship between wavelength and normalized intensity that is obtained by dividing the intensity at each of the plurality of wavelengths by an average of an intensity in a predetermined wavelength range.

8. The method according to claim 1, wherein the substrate is a second substrate to be polished after a first substrate having a same structure, and
said method further comprises:
directing light to the first substrate during polishing of the first substrate;
receiving reflected light from the first substrate;
measuring an intensity of the reflected light at each of a plurality of wavelengths;
producing reference spectrum indicating a relationship between intensity and wavelength from measured values of the intensity;
calculating an amount of change in the reference spectrum per predetermined time;
integrating the amount of change in the reference spectrum with respect to polishing time to obtain an amount of cumulative change in the reference spectrum; and
converting the amount of cumulative change in the spectrum with respect to the second substrate into an amount of removed film of the second substrate based on the amount of cumulative change in the reference spectrum, an initial film thickness of the first substrate, and a final film thickness of the first substrate.

9. The method according to claim 8, further comprising:
obtaining an initial film thickness of the second substrate; and
converting the amount of removed film into a film thickness of the second substrate by subtracting the amount of removed film from the initial film thickness of the second substrate.

10. The method according to claim 1, wherein said polishing of the substrate is polishing of the substrate for adjusting a height of metal interconnects formed in the substrate.

11. The method according to claim 10, wherein:
the substrate has the film, a barrier layer formed on the film, and the metal interconnects formed in the film; and
said method further comprises determining a removal point of the barrier layer based on the amount of change in the spectrum.

12. The method according to claim 1, wherein:
the substrate has a surface having steps formed thereon; and
said calculating of the amount of change in the spectrum is started from a point of time when the steps are removed.

13. The method according to claim 1, further comprising:
determining a polishing end point of the substrate based on the amount of cumulative change in the spectrum.

14. A method of polishing a substrate having a film, said method comprising:
polishing the substrate by providing sliding contact between the substrate and a polishing pad;
directing light to the substrate during said polishing of the substrate;
receiving reflected light from the substrate;
measuring an intensity of the reflected light at each of a plurality of wavelengths;
producing spectrum indicating a relationship between intensity and wavelength from measured values of the intensity;
calculating an amount of change in the spectrum per predetermined time;
integrating the amount of change in the spectrum with respect to polishing time to obtain an amount of cumulative change in the spectrum; and
monitoring progress of polishing of the substrate based on the amount of cumulative change in the spectrum.

15. The method according to claim 14, wherein the amount of change in the spectrum is a magnitude of relative change between two spectra produced at two different points of time.

16. The method according to claim 15, wherein the magnitude of relative change is a root mean square of a difference in intensity between the two spectra in a predetermined wavelength range.

17. The method according to claim 15, wherein the magnitude of relative change is an average of absolute values of a difference in intensity between the two spectra in a predetermined wavelength range.

18. The method according to claim 15, wherein the amount of change in the spectrum is a rate of change in the spectrum obtained by dividing the magnitude of relative change by a time interval between the two different points of time.

19. The method according to claim 14, wherein the amount of change in the spectrum has a plus or minus sign.

20. The method according to claim 14, wherein the spectrum is a spectrum indicating relationship between wavelength and normalized intensity that is obtained by dividing the intensity at each of the plurality of wavelengths by an average of an intensity in a predetermined wavelength range.

21. The method according to claim 14, wherein the substrate is a second substrate to be polished after a first substrate having a same structure, and
said method further comprises:
directing light to the first substrate during polishing of the first substrate;
receiving reflected light from the first substrate;
measuring an intensity of the reflected light at each of a plurality of wavelengths;
producing reference spectrum indicating a relationship between intensity and wavelength from measured values of the intensity;
calculating an amount of change in the reference spectrum per predetermined time;
integrating the amount of change in the reference spectrum with respect to polishing time to obtain an amount of cumulative change in the reference spectrum; and
converting the amount of cumulative change in the spectrum with respect to the second substrate into an amount of removed film of the second substrate based on the amount of cumulative change in the reference spectrum, an initial film thickness of the first substrate, and a final film thickness of the first substrate.

22. The method according to claim 21, further comprising:
obtaining an initial film thickness of the second substrate; and
converting the amount of removed film into a film thickness of the second substrate by subtracting the amount of removed film from the initial film thickness of the second substrate.

23. The method according to claim 14, wherein said polishing of the substrate is polishing of the substrate for adjusting a height of metal interconnects formed in the substrate.

24. The method according to claim 23, wherein:
the substrate has the film, a barrier layer formed on the film, and the metal interconnects formed in the film; and
said method further comprises determining a removal point of the barrier layer based on the amount of change in the spectrum.

25. The method according to claim 14, further comprising:
terminating said polishing of the substrate when the amount of cumulative change in the spectrum has reached a predetermined target value.

26. The method according to claim 14, further comprising:
determining a point of time when steps, which are formed on a surface of the substrate, are removed by said polishing of the substrate,
wherein said calculating of the amount of change in the spectrum is started from the point of time when the steps are removed.

27. A polishing monitoring apparatus, comprising:
a light-applying unit configured to direct light to a substrate during polishing of the substrate;
a light-receiving unit configured to receive reflected light from the substrate;
a spectroscope configured to measure an intensity of the reflected light at each of a plurality of wavelengths; and
a processing device configured to process measurement data from said spectroscope,
wherein said processing device is configured to
produce a spectrum indicating relationship between intensity and wavelength from measured values of the intensity,
calculate an amount of change in the spectrum per predetermined time,
integrate the amount of change in the spectrum with respect to polishing time to obtain an amount of cumulative change in the spectrum, and
monitor the progress of polishing of the substrate based on the amount of cumulative change in the spectrum.

28. A non-transitory computer readable medium having a program stored thereon for enabling a computer to execute a method comprising:
producing spectrum indicating a relationship between intensity and wavelength of reflected light from a substrate;
calculating an amount of change in the spectrum per predetermined time;
integrating the amount of change in the spectrum with respect to polishing time to obtain an amount of cumulative change in the spectrum; and
monitoring progress of polishing of the substrate based on the amount of cumulative change in the spectrum.

* * * * *